United States Patent
Hilmer et al.

(10) Patent No.: US 9,359,622 B2
(45) Date of Patent: Jun. 7, 2016

(54) METHOD FOR BIOTECHNOLOGICAL PRODUCTION OF DIHYDROCHALCONES

(71) Applicant: Symrise AG, Holzminden (DE)

(72) Inventors: Jens Michael Hilmer, Holzminden (DE); Egon Gross, Holzminden (DE); Gerhard Krammer, Holzminden (DE); Jakob Peter Ley, Holzminden (DE); Mechthild Gall, Greifswald (DE); Uwe Bornscheuer, Griefswald (DE); Maren Thomsen, Greifswald (DE); Christin Peters, Greifswald (DE); Patrick Jonczyk, Hannover (DE); Sascha Beutel, Hannover (DE); Thomas Scheper, Hannover (DE)

(73) Assignee: SYMRISE AG, Holzminden (DE)

( * ) Notice: Subject to any disclaimer, the term of this patent is extended or adjusted under 35 U.S.C. 154(b) by 48 days.

(21) Appl. No.: 13/954,957

(22) Filed: Jul. 30, 2013

(65) Prior Publication Data
US 2014/0045233 A1 Feb. 13, 2014

(30) Foreign Application Priority Data
Jul. 31, 2012 (DE) .......................... 10 2012 213 492

(51) Int. Cl.
| | |
|---|---|
| *C12P 7/26* | (2006.01) |
| *C12N 1/21* | (2006.01) |
| *C12N 9/02* | (2006.01) |
| *C12N 9/90* | (2006.01) |
| *C12N 15/53* | (2006.01) |
| *C12N 15/61* | (2006.01) |
| *C12N 15/63* | (2006.01) |
| *C12R 1/01* | (2006.01) |
| *C12R 1/19* | (2006.01) |
| *C12R 1/645* | (2006.01) |
| *C12R 1/865* | (2006.01) |
| *C12R 1/84* | (2006.01) |

(52) U.S. Cl.
CPC . *C12P 7/26* (2013.01); *C12N 9/001* (2013.01); *C12N 9/90* (2013.01); *C12R 1/01* (2013.01); *C12R 1/19* (2013.01); *C12R 1/645* (2013.01); *C12R 1/84* (2013.01); *C12R 1/865* (2013.01); *C12Y 103/01031* (2013.01); *C12Y 505/01006* (2013.01); *Y02P 20/52* (2015.11)

(58) Field of Classification Search
None
See application file for complete search history.

(56) References Cited

U.S. PATENT DOCUMENTS

2005/0208643 A1  9/2005  Schmidt-Dannert et al.

OTHER PUBLICATIONS

Chaparro-Riggers et al., Comparison of Three Enoate Reductases and their Potential Use for Biotransformations, Adv. Synth. Catal., 2007, 349, 1521-31.*
Ngaki et al., Evolution of the chalcone-isomerase fold from fatty-acid binding to stereospecific catalysis, Nature, May 2012, 485, 530-33 and Supplemental Information.*
Baldock et al., A Mechanism of Drug Action Revealed by Structural Studies of Enoyl Reductase, Science, 1996, 274, 2107-10.*
Uniprot, Accession No. V9P0A9, 2014, www.uniprot.org.*
Uniprot, Accession No. V9P074, 2014, www.uniprot.org.*
European Search Report dated Sep. 30, 2013.
Schmidt, et al., "Biocatalytic Formation of a Bioactive Dihydrochalcone by Eubacterium Ramulus," Journal of Biotechnology, Elsevier Science Publishers, Amsterdam, NL, BD. 150, Nov. 1, 2010, p. 150, XP027489759.
Schneider, et al., "Anaerobic Degradation of Flavonoids by Eubacterium Ramulus," Archives of Microbiology, Springer, DE, Bd. 173, Nr.1, Jan. 1, 2000, pp. 71-75, XP008115183.
Herles, et al., "First Bacterial Chalcone Isomerase isolated from Eubacterium Ramulus," Archives of Microbiology, Bd. 181, Nr. 6, Jun. 2004, pp. 428-434, XP002713878.
Hwang, et al., "Production of Plant-Specific Flavonones by *Escherichia coli* Containing an Artificial Gene Cluster," Applied and Environmental Microbiology, American Society for Microbiology, US, Bd. 69, Nr. 5, May 1, 2003, pp. 2699-2706, XP008117399.
Databse UniProt, Feb. 1, 1995, "RecName: Full=Chalcone—flavonone isomerase 1; Short=Chalcone isomerase 1; EC=5.5..1.6; AltName: Full=Protein Transparent Testa 5." XP002713879.

* cited by examiner

*Primary Examiner* — Robert Mondesi
*Assistant Examiner* — Todd M Epstein
(74) *Attorney, Agent, or Firm* — Polsinelli PC

(57) ABSTRACT

A method for production of a dihydrochalcone, especially of phloretin, using a transgenic microorganism, containing a nucleic acid section (a), comprising or consisting of a gene coding for a bacterial chalcone isomerase, and/or a nucleic acid section (a'), comprising or consisting of a gene coding for a plant chalcone isomerase, and a nucleic acid section (b), comprising or consisting of a gene coding for a bacterial enoate reductase, corresponding transgenic microorganisms, containing a nucleic acid section (a), comprising or consisting of a gene coding for a bacterial chalcone isomerase, and/or a nucleic acid section (a'), comprising or consisting of a gene coding for a plant chalcone isomerase, and/or a nucleic acid section (b), comprising or consisting of a gene coding for a bacterial enoate reductase, and host cells, containing one or more identical or different such vectors.

39 Claims, 6 Drawing Sheets

METHOD FOR BIOTECHNOLOGICAL PRODUCTION OF DIHYDROCHALCONES

CROSS-REFERENCE TO RELATED APPLICATIONS

This application claims the benefit of DE Patent Application Serial No. 10 2012 213 492.1, filed on 31 Jul. 2012, the benefit of the earlier filing date of which is hereby claimed under 35 USC §119(a)-(d) and (f). The application is hereby incorporated in its entirety as if fully set forth herein.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Substitute_Sequence_Listing_34430_7. The size of the text file is 22 KB, and the text file was created on Dec. 3, 2015.

BACKGROUND OF THE INVENTION

1. Field of the Invention

The present invention primarily concerns a method for production of a dihydrochalcone, especially of phloretin, or a method for reduction of flavanones using a transgenic microorganism, containing a nucleic acid section (a), comprising or consisting of a gene coding for a bacterial chalcone isomerase, and/or a nucleic acid section (a'), comprising or consisting of a gene coding for a plant chalcone isomerase, and a nucleic acid section (b), comprising or consisting of a gene coding for a bacterial enoate reductase.

2. Description of Related Art

Dihydrochalcones, especially phloretin, are normally produced either by chemical reduction of chalcones or by Friedel-Crafts acylation of phenols with dihydrocinammic acids. The disadvantage of this method is that food additives, flavourings or aromatic substances produced in this way cannot be described as natural. In addition, dihydrochalcones, especially phloretin, can be obtained by extraction of for example the corresponding glycoside (E. g. from *Malus* spp. raw materials) with subsequent generation of the aglycone. This process is time-consuming and cost-intensive, however, and is also dependent on the season.

Important flavourings and aromatic substances with a dihydrochalcone structure are for example phloretin (E. g. according EP 1,998,636-B1), phloridzin, trilobtain (see Tanaka, T.; Yamasaki, K.; Kohda, H.; Tanaka, O.; Mahato, S. B., Dihydrochalcone-glucosides as sweet principles of *Symplocos* ssp. *Planta Medica* 1980, (Suppl.), 81-83), naringin dihydrochalcone and neohesperidine dihydrochalcone (Crosby, G. A., New Sweeteners. *Critical Reviews in Food Science and Nutrition* 1976, (June), 297-323).

Due to the existing and also the future need for advantageous dihydrochalcones, especially for phloretin, the primary problem for the present invention was to provide an efficient and preferably cost-effective that can be used on an industrial scale for producing dihydrochalcones, especially phloretin.

A further problem was to provide suitable or necessary means for performing such a method.

Further problems for the present invention are apparent from the following description and especially the attached claims.

These and other objects, features, and advantages of the present invention will become more apparent upon reading the following specification in conjunction with the accompanying drawing figures.

Further aspects of the present invention and preferred configurations thereof can be seen from the following description, the exemplary embodiments and the claims.

DETAILED DESCRIPTION OF THE PREFERRED EMBODIMENTS

Figure 1:
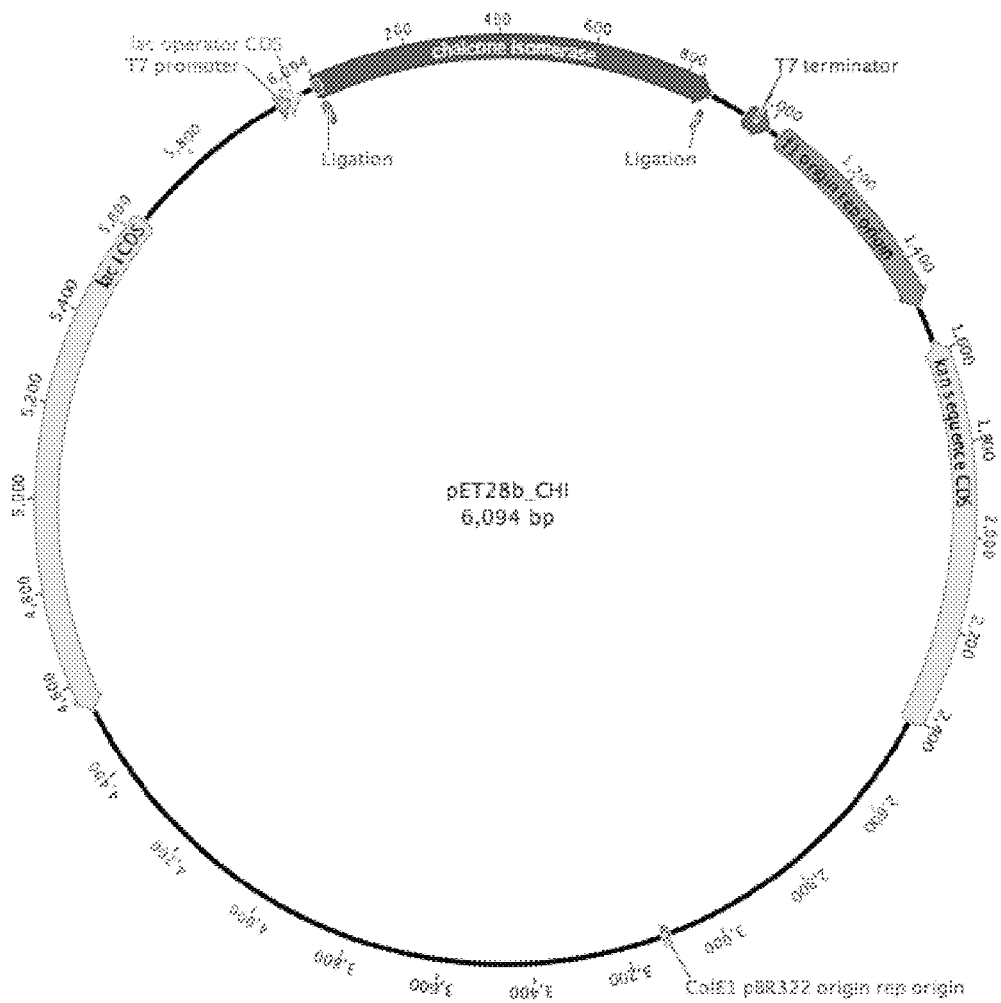
FIG. 1: Plasmid pET52b_EREDstrep for heterologous expression and characterization of the ERED from *E. ramulus* DSM 16296.

To facilitate an understanding of the principles and features of the various embodiments of the invention, various illustrative embodiments are explained below. Although exemplary embodiments of the invention are explained in detail, it is to be understood that other embodiments are contemplated. Accordingly, it is not intended that the invention is limited in its scope to the details of construction and arrangement of components set forth in the following description or illustrated in the drawings. The invention is capable of other embodiments and of being practiced or carried out in various ways. Also, in describing the exemplary embodiments, specific terminology will be resorted to for the sake of clarity.

It must also be noted that, as used in the specification and the appended claims, the singular forms "a," "an" and "the" include plural references unless the context clearly dictates otherwise. For example, reference to a component is intended also to include composition of a plurality of components. References to a composition containing "a" constituent is intended to include other constituents in addition to the one named.

Also, in describing the exemplary embodiments, terminology will be resorted to for the sake of clarity. It is intended that each term contemplates its broadest meaning as understood by those skilled in the art and includes all technical equivalents which operate in a similar manner to accomplish a similar purpose.

Ranges may be expressed herein as from "about" or "approximately" or "substantially" one particular value and/or to "about" or "approximately" or "substantially" another particular value. When such a range is expressed, other exemplary embodiments include from the one particular value and/or to the other particular value.

Similarly, as used herein, "substantially free" of something, or "substantially pure", and like characterizations, can include both being "at least substantially free" of something, or "at least substantially pure", and being "completely free" of something, or "completely pure".

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified. Similarly, it is also to be understood that the mention of one or more components in a composition does not preclude the presence of additional components than those expressly identified.

The materials described as making up the various elements of the invention are intended to be illustrative and not restrictive. Many suitable materials that would perform the same or a similar function as the materials described herein are intended to be embraced within the scope of the invention. Such other materials not described herein can include, but are not limited to, for example, materials that are developed after the time of the development of the invention.

The present invention primarily concerns a method for production of a dihydrochalcone, especially of phloretin, or a method for reduction of flavanones using a transgenic microorganism, containing a nucleic acid section (a), comprising or consisting of a gene coding for a bacterial chalcone isomerase, and/or a nucleic acid section (a'), comprising or consisting of a gene coding for a plant chalcone isomerase, and a nucleic acid section (b), comprising or consisting of a gene coding for a bacterial enoate reductase.

The present invention further concerns a transgenic microorganism, containing a nucleic acid section (a), comprising or consisting of a gene coding for a bacterial chalcone isomerase, and/or a nucleic acid section (a'), comprising or consisting of a gene coding for a plant chalcone isomerase, and a nucleic acid section (b), comprising or consisting of a gene coding for a bacterial enoate reductase.

The present invention also concerns a vector, especially a plasmid vector, containing a nucleic acid section (a), comprising or consisting of a gene coding for a bacterial chalcone isomerase, and/or a nucleic acid section (a'), comprising or consisting of a gene coding for a plant chalcone isomerase, and/or a nucleic acid section (b), comprising or consisting of a gene coding for a bacterial enoate reductase.

In addition, the present invention concerns a host cell, containing one or more identical or different vectors according to the invention.

Further aspects of the invention are apparent from the following description, the examples and especially the attached claims.

The primary problem for the present invention is solved by an innovative biotechnological method for producing a dihydrochalcone, especially phloretin, using a transgenic microorganism, comprising the following steps:

(i) Providing a transgenic microorganism, containing (as the transgene)
    a nucleic acid section (a), comprising or consisting of a gene coding for a bacterial chalcone isomerase,
    and/or a nucleic acid section (a'), comprising or consisting of a gene coding for a plant chalcone isomerase, and
    a nucleic acid section (b), comprising or consisting of a gene coding for a bacterial enoate reductase.

(ii) Adding one or more flavanones, especially adding naringin, and/or one or more one or more precursors or one or more derivatives thereof, especially a precursor or a derivative of naringin, to the transgenic microorganism and cultivation of the transgenic microorganism under conditions which allow the conversion of the flavanone(s) and/or precursor(s) or derivative(s) thereof, especially naringin and/or the precursor or derivative of naringin, into a dihydrochalcone, especially into phloretin.

(iii) Optionally: isolating and if necessary purifying the dihydrochalcone, especially phloretin.

The or one, more or all the flavanones or precursors or derivatives thereof to be used according to the invention are preferably selected from the group consisting of:

naringenin, naringin, narirutin, or other naringenin glycosides, hesperetin, hesperidin, neohesperidin, hesperetin-7-O-glucoside, or other hesperetin glycosides, eriodictyol, eriocitrin, or other eriodictyol glycoside, sterubin, sterubin glycoside, sakuranetin, sakuranetin glycosides, isosakuranetin, isosakuranetin glycosides, 4',7-dihydroxy-flavanone or glycosides thereof, 4',7-dihydroxy-3'-methoxy-flavanone or glycosides thereof, 3',7-dihydroxy-4'-methoxy-flavanone or glycosides thereof, 3',4',7-trihydroxy-flavanone or glycosides thereof, wherein the flavanones with regard to the 2-position of the flavanone structure can be present as (S)-, as (R)-enantiomer, as racemate or as any mixture of the two enantiomers.

In the following examples are provided of a number of flavanones that are used by preference:

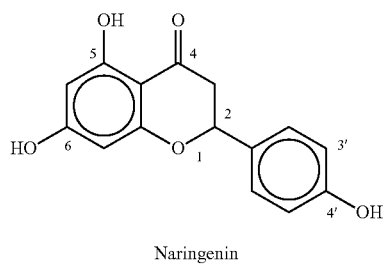
Naringenin

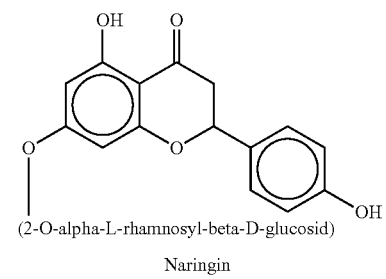
(2-O-alpha-L-rhamnosyl-beta-D-glucosid)
Naringin

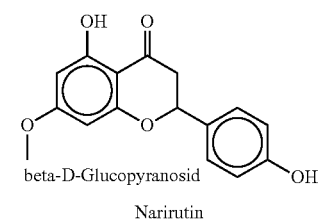
Narirutin

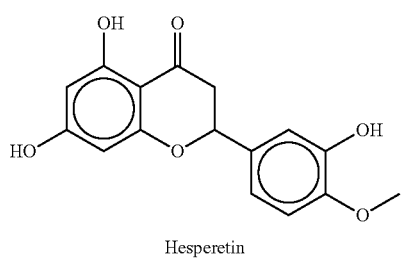
Hesperetin

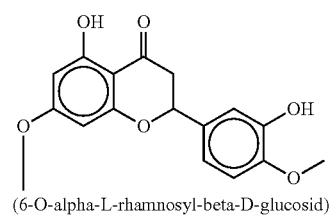
(6-O-alpha-L-rhamnosyl-beta-D-glucosid)
Hesperidin

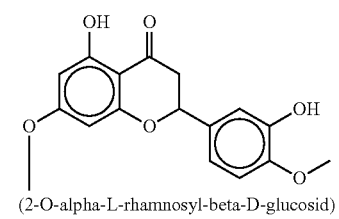
(2-O-alpha-L-rhamnosyl-beta-D-glucosid)
Neohesperidin

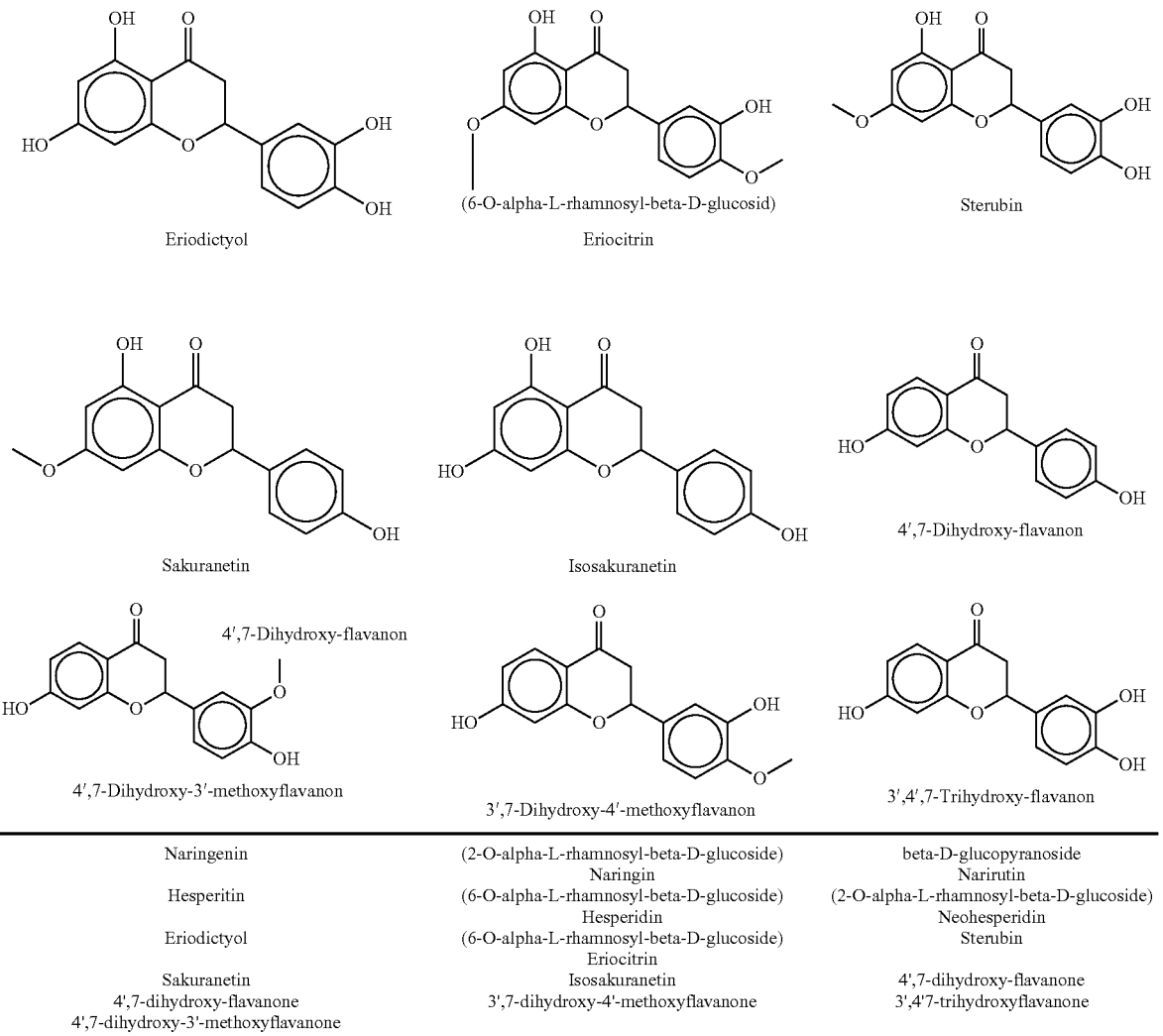

The dihydrochalcone to be produced according to the invention is preferably selected from the group consisting of: phloretin, naringin dihydrochalcone, phloridzin or other phloretin-glycosides, hesperetin dihydrochalcone, hesperidin dihydrochalcone, neohesperidine dihydrochalcone, or other hesperetin dihydrochalcone glycosides, eriodictyol dihydrochalcone (3-hydroxyphloretin), or other eriodictyol dihydrochalcone glycosides, sterubin dihydrochalcone, sterubin dihydrochalcone glycoside, sakuranetin dihydrochalcone, sakuranetin dihydrochalcone glycosides, isosakuranetin dihydrochalcone, isosakuranetin dihydrochalcone glycosides, 2',4',4-trihydroxydihydrochalcone (davidigenin) or glycosides thereof, 3-methoxy-2',4',4-trihydroxydihydrochalcone or glycosides thereof, 4-methoxy-2',3,4'-trihydroxydihydrochalcone or glycosides thereof or 2',4,4',3-tetrahydroxydihydrochalcone or glycosides thereof.

In the following examples are provided of preferred dihydrochalcones:

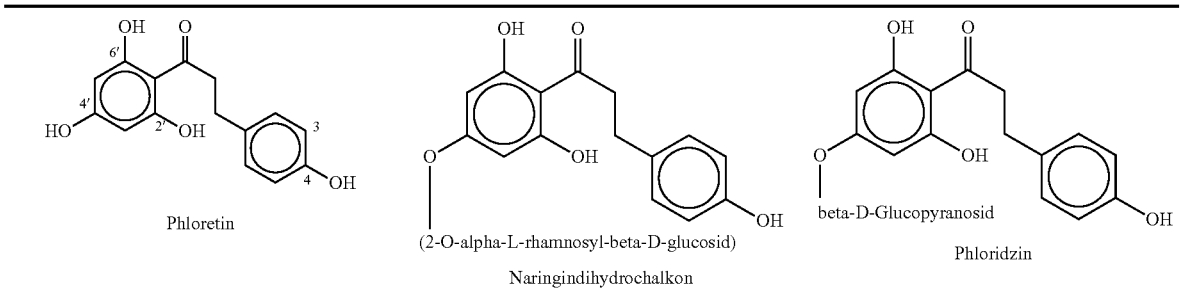

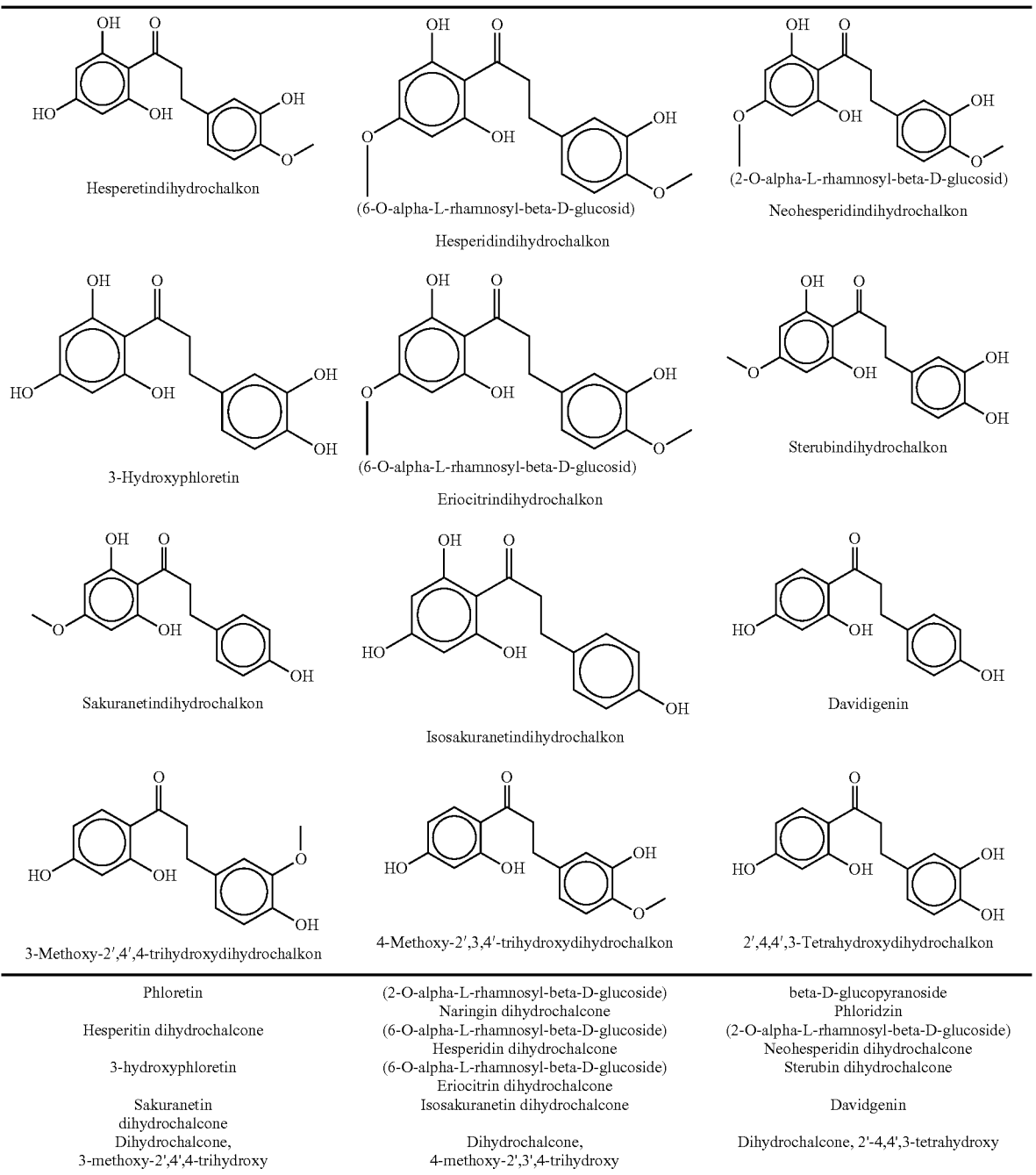

Especially preferred flavanones and the respective dihydrochalcones formed from these are: naringenin and phloretin, naringin and naringin dihydrochalcone, narirutin and phloridzin, hesperetin and hesperetin dihydrochalcone, hesperidin and hesperidin dihydrochalcone, neohesperidin and neohesperidine dihydrochalcone, and eriodictyol and 3-hydroxyphloretin.

A first aspect of the present invention accordingly concerns a biotechnological method for production of (natural) dihydrochalcones, especially of (natural) phloretin, starting from one or more corresponding flavanones and/or a precursor or a derivative thereof, especially of naringin and/or a precursor or a derivative of naringin, especially of naringin or naringenin, using a bacterial chalcone isomerase (especially preferably from microorganisms as described further below) and/or a plant chalcone isomerase (especially preferably from plants as described further below) in combination with a bacterial enoate reductase (preferably from microorganisms as described below) in a transgenic microorganism.

A preferred embodiment concerns a biotechnological method for production of (natural) phloretin, starting from naringin and/or a precursor or a derivative of naringin, especially of naringin, narirutin or naringenin, using one or more chalcone isomerases (as described herein) in combination with an enoate reductase (as described herein) using a transgenic microorganism (as similarly described herein).

An especially preferred embodiment concerns a biotechnological method for the production of (natural) phloretin, starting from naringin and/or a precursor or a derivative of naringin, especially of naringin, narirutin or naringenin, using a bacterial chalcone isomerase (preferably from the anaerobic organism *Eubacterium ramulus*, as described further below) in combination with plant chalcone isomerase (preferably from *Arabidopsis thaliana* or *Medicago sativa*, as described further below) and a bacterial enoate reductase (similarly preferably from the anaerobic organism *Eubacterium ramulus*, as described further below) using a transgenic microorganism (as described herein).

In the state of the art it was known that the anaerobic microorganism *Eubacterium ramulus* is able to degrade naringenin, wherein intermediate phloretin is formed. However, this is not understood to be a (biotechnological) method for production of phloretin within the meaning of the present invention, especially not a method (as described above), suitable for the industrial production of phloretin, E. g. for production of phloretin on an industrial scale. For the intermediate phloretin formed is immediately further metabolised into *Eubacterium ramulus*(see Schneider et al, Anaerobic degradation of flavonoids by *Eubacterium ramulus*, Arch Microbiol (2000) 173: 71-75), as shown in the following reaction diagram, (see especially the reaction brought about by the phloretin hydrolase (PhH)):

yeasts (E. g. *saccharomyces*). To date there has been little research into enzymatic ether splitting, however.

In connection with the present invention, reference is basically made to the following publications: Schoefer et al, Anaerobic Degradation of Flavonoids by *Clostridium orbiscindens*, Appl. Environ. Microbiol., October 2003, p. 5849-5854; and Herles et al, First bacterial chalcone isomerase isolated from *Eubacterium ramulus*, Arch Microbiol (2004) 181: 428-434. Findings in connection with the degradation of lignin have for example been described by Masai et al. (Masai et al., 1993; Otsuka et al., 2003; see also JP 2002034557).

In WO 2006010117 from Koffas et al. and WO 2005084305 from Schmidt-Dannert et al. the application of heterologous expression for the formation of flavonoids is described. In these (exclusively) plant genes are described, which can be used for heterologous expression of various substances (starting from L-phenylalanine, tyrosine and cinnamic acid).

Surprisingly, by means of the genome sequence of *Eubacterium ramulus* the gene coding (a) for a chalcone isomerase and (b) for an enoate reductase (for conversion of naringin or a precursor a derivative of naringin to phloretin; see on this point the reaction diagram shown above) could be identified and thereupon expressed in transgenic microorganisms. The heterologous expression of this enzyme in a transgenic microorganism is able to advantageously avoid or circumvent

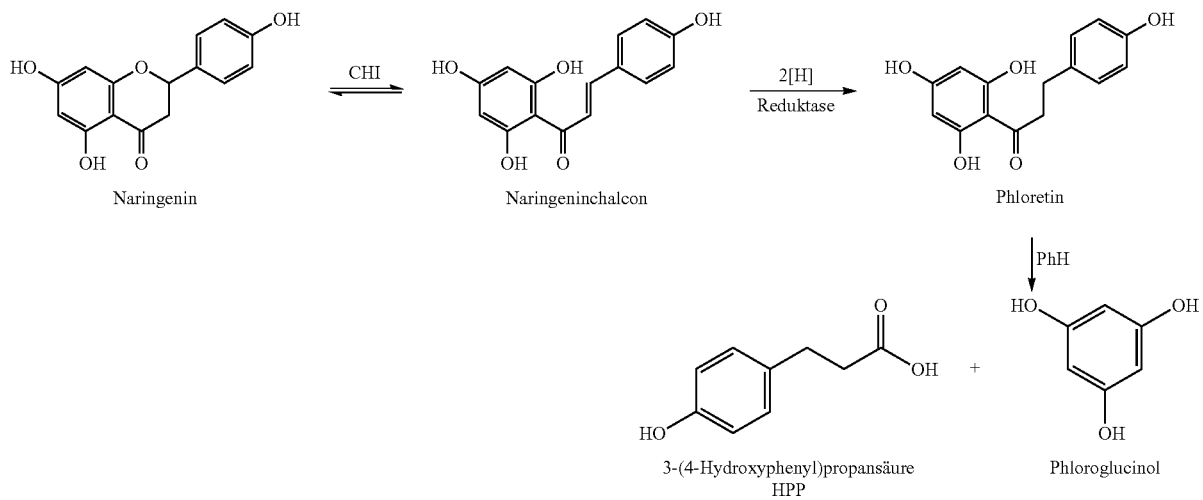

Naringinin
Naringinin chalcone
Reductase
Phloretin
pHH
3-(4-hydroxyphenyl)propanic acid HPP
Phloroglucinol In the context of the investigations in connection with the present invention it was possible for the purposes of the method described herein to clarify and characterize crucial molecular biological and biochemical principles of the biotransformation, for the purposes of production of phloretin on an industrial scale (without immediate degrading of the phloretin formed).

In the state of the art a number of different possibilities for use of enzyme systems and methods of microbial biotransformation are indeed described; for example, it is known to be possible for double bonds to be simply reduced by means of the secondary reaction that normally takes place in *E. ramulus* of phloretin to phloroglucinol and 3-(4-hydroxyphenyl) propanic acid (HPP) through the phloretin hydrolase (on this point see the reaction diagram shown above), in order ultimately to allow the production of phloretin on an industrial scale or a significant increase in product yield.

A "transgenic microorganism" in connection with the present invention is understood to be a genetically engineered or modified microorganism, in which specifically through biotechnological methods nucleic acid sections (see nucleic acid sections (a) and (b) as described herein) or genes are introduced into another organism (so-called transgene).

A "chalcone isomerase" (CHI) within the meaning of the present invention is an enzyme that catalyses the "chalcone⇌flavanone" reaction. CHI especially catalyses the reaction of/to naringenin to/of naringenin chalcone (see the reaction diagram shown above), for the purposes of the present invention especially the reaction of naringenin to naringenin chalcone.

An "enoate reductase" (ERED) within the meaning of the present invention is an enzyme, that catalyses the dehydration of certain compounds especially the reaction of naringenin chalcone to phloretin (see the reaction diagram shown above).

In view of the relationships explained above, the transgenic microorganism used in connection with the method according to the invention is in particular not *Eubacterium ramulus*, in particular not a microorganism of the Clostridiales order, more preferably not a microorganism of the Clostridia class, especially preferably not a microorganism of the phylum (section) of Firmicutes. Rather, the microorganism is preferably selected from the group consisting of facultative anaerobic microorganisms, especially facultative aerobic bacteria, preferably proteobacteria, especially enterobacteria, for example of the genus *Escherichia*, preferably *E. coli*, especially *E. coli* BL21, *E. coli* Rosetta (derivative of *E. coli* BL 21) and *E. coli* SE1, and yeasts, for example *S. cerevesiae* and *P. pastoris*. According to a preferred aspect for the purposes of the invention described herein basically those microorganisms are preferred which grow under aerobic conditions and (also) under exclusion of oxygen are able to express the introduced gene (transgene; see above).

Preference according to the invention is for a method (as described above), wherein in step (ii) naringin and/or an aglycone thereof is or are added.

Coding in particular takes place as follows the gene coding for a bacterial chalcone isomerase for a chalcone isomerase from a microorganism from the phylum Firmicutes, in particular the Clostridia class, especially of the Clostridiales order, especially preferably for a chalcone isomerase from *E. ramulus*, and/or the gene coding for a plant chalcone isomerase for a chalcone isomerase from a plant of the order Brassicales, in particular from the family of Brassicaceae, preferably the tribe Camelineae, especially the genus *Arabidopsis*, above all of the type *Arabidopsis thaliana*, or the order Fabales, in particular the family Fabaceae, preferably the sub-family Faboidae, especially the genus *Medicago*, above all of the type *Medicago sativa*, thus especially preferably for a chalcone isomerase from *A. thaliana* or *M. sativa* (see on this point WO2005084305 A2 (Schmidt-Dannert) and WO2006010117A2 (Koffas)), and/or the gene coding for a bacterial enoate reductase for an enoate reductase from a microorganism from the phylum Firmicutes, in particular the class Clostridia, especially the order Clostridiales, especially preferably for an enoate reductase from *E. ramulus*.

Especially preferable is a method according to the invention (as described herein), wherein the nucleic acid section (a) is comprised or consists of a nucleotide sequence according to SEQ ID NO:1 (nucleotide sequence of the gene coding for the bacterial CHI from *E. ramulus* DSM 16296) or a nucleotide sequence with a nucleotide sequence identity of 40% or more for SEQ ID NO:1, in particular of 50% or more, 60% or more or 80% or more, especially preferably of 95% or more, and/or the nucleic acid section (a') is comprised or consists of a nucleotide sequence according to SEQ ID NO:6 (nucleotide sequence of the CHI from *M. sativa* (cultivar Iroquois) (Ms-CHI-1) mRNA, complete cds) or SEQ ID NO:7 (nucleotide sequence of the chalcone flavanone isomerase 1 (TT5) mRNA from *Arabidopsis thaliana*, complete cds) or a nucleotide sequence with a nucleotide sequence identity of 40% or more for SEQ ID NO:6 or SEQ ID NO:7, in particular of 50% or more, 60% or more or 80% or more, especially preferably of 95% or more, and/or the nucleic acid section (b) is comprised or consists of a nucleotide sequence according to SEQ ID NO:2 (nucleotide sequence of the gene coding for the bacterial ERED from *E. ramulus* DSM 16296) or SEQ ID NO:5 (codon optimised nucleotide sequence of the gene coding for bacterial ERED from *E. ramulus* DSM 16296, especially for expression in *E. coli* BL21, integrated in pET 22b (clones by means of Nde1 and BamH1)) or a nucleotide sequence with a nucleotide sequence identity of 40% or more for SEQ ID NO:2 or SEQ ID NO:5, in particular of 50% or more, 60% or more or 80% or more, especially preferably of 95% or more.

Preference according to the invention is further for a method (as described above), wherein the bacterial chalcone isomerase is comprised or consists of an amino acid sequence according to SEQ ID NO:3 (amino acid sequence of the bacterial CHI from *E. ramulus* DSM 16296) or an amino acid sequence with an amino acid sequence identity of 40% or more for SEQ ID NO:3, in particular of 50% or more, 60% or more or 80% or more, especially preferably of 95% or more, and/or the plant chalcone isomerase is comprised or consists of an amino acid sequence according to SEQ ID NO:8 (amino acid sequence of the chalcone isomerase from *Medicago sativa*) or SEQ ID NO:9 (amino acid sequence of the chalcone flavanone isomerase 1 from *Arabidopsis thaliana*) or an amino acid sequence with an amino acid sequence identity of 40% or more for SEQ ID NO:8 or SEQ ID NO:9, in particular of 50% or more, 60% or more or 80% or more, especially preferably of 95% or more, and/or the bacterial enoate reductase is comprised or consists of an amino acid sequence according to SEQ ID NO:4 (amino acid sequence of the bacterial ERED from *E. ramulus* DSM 16296) or an amino acid sequence with an amino acid sequence identity of 40% or more for SEQ ID NO:4, in particular of 50% or more, 60% or more or 80% or more, especially preferably of 95% or more.

In the context of the present invention the "amino acid sequence identity" is preferably determined using the Waterman-Smith algorithm with a gap open penalty of 10, a gap extension penalty of 0.5 and the BLOSUM62 matrix (regarding the Waterman-Smith algorithm, see for example Smith, T. F. and Waterman, M. S., Identification of common molecular subsequences, Journal of Molecular biology (1981), 147: 195-197; implemented online via the corresponding tool page of the EMBL).

For the purposes of the present invention especially preferred is the use of a chalcone isomerase, having one, several or all the following characteristics and/or a temperature and pH stability according to Tables 1-3:

| $K_M$ [µmol/l] | $V_{max}$ [U/mg] | $k_{cat}$ [s$^{-1}$] | $k_{cat}/K_M$ [l * mol$^{-1}$ * s$^{-1}$] |
|---|---|---|---|
| 36.83 | 107.3 | 416.7 | 1.13 * 10$^7$ |

TABLE 1 activity measurements for determination of the
temperature optimum for CHI

| Temperature | Spec. activity [U/mg] | Standard deviation |
|---|---|---|
| RT (23° C.) | 158.39 | 26.19 |
| 30° C. | 373.47 | 5.77 |
| 37° C. | 795.04 | 45.62 |
| 40° C. | 887.73 | 37.95 |
| 45° C. | 1133.38 | 76.26 |
| 50° C. | 748.66 | 37.37 |

TABLE 2 for temperature stability:

| Temp | Time [h] | Spec. activity [U/mg] | Standard deviation |
|---|---|---|---|
| RT (23° C.) | 0 | 188.56 | 1.97 |
|  | 0.5 | 145.67 | 2.61 |
|  | 1 | 148.67 | 6.89 |
|  | 2 | 144.05 | 2.04 |
|  | 4 | 146.39 | 2.85 |
|  | 6 | 141.06 | 2.64 |
|  | 24 | 125.68 | 1.44 |
| 25° C. | 0 | 188.56 | 1.97 |
|  | 0.5 | 136.70 | 2.89 |
|  | 1 | 141.10 | 1.25 |
|  | 2 | 152.08 | 2.61 |
|  | 4 | 152.48 | 1.71 |
|  | 6 | 146.46 | 1.38 |
|  | 24 | 116.37 | 0.22 |
| 30° C. | 0 | 188.56 | 1.97 |
|  | 0.5 | 169.66 | 9.66 |
|  | 1 | 158.01 | 7.76 |
|  | 2 | 154.62 | 3.50 |
|  | 4 | 145.77 | 1.63 |
|  | 6 | 147.18 | 4.45 |
|  | 24 | 119.96 | 1.14 |
| 37° C. | 0 | 188.56 | 1.97 |
|  | 0.5 | 155.20 | 0.44 |
|  | 1 | 164.39 | 3.68 |
|  | 2 | 156.17 | 1.87 |
|  | 4 | 156.84 | 0.38 |
|  | 6 | 156.21 | 3.88 |
|  | 24 | 93.93 | 3.89 |
| 41° C. | 0 | 188.56 | 1.97 |
|  | 0.5 | 151.96 | 1.19 |
|  | 1 | 154.22 | 0.50 |
|  | 2 | 149.12 | 0.57 |
|  | 4 | 146.59 | 2.73 |
|  | 6 | 149.39 | 3.36 |
|  | 24 | 93.30 | 2.71 |
| 44° C. | 0 | 188.56 | 1.97 |
|  | 0.5 | 158.12 | 0.52 |
|  | 1 | 150.15 | 0.34 |
|  | 2 | 129.07 | 0.75 |
|  | 4 | 115.07 | 0.24 |
|  | 6 | 83.35 | 6.13 |
| 50° C. | 0 | 188.56 | 1.97 |
|  | 0.5 | 50.49 | 5.61 |
|  | 1 | 3.05 | 1.55 |
|  | 2 | 2.35 | 0.63 |

TABLE 3 of results of the activity measurements for
determination of the pH optimum

| pH value | Spec. activity [U/mg] | Standard deviation |
|---|---|---|
| 6.13 | 82.07 | 5.97 |
| 6.35 | 163.43 | 5.62 |
| 6.4 | 177.59 | 2.44 |
| 6.55 | 169.79 | 1.38 |
| 6.8 | 185.86 | 2.46 |
| 6.93 | 175.37 | 2.47 |
| 7.12 | 174.86 | 1.15 |
| 7.45 | 173.01 | 1.73 |
| 7.7 | 168.79 | 1.37 |
| 8 | 152.55 | 5.97 |

For the purposes of the present invention preference is for the use of an enoate reductase, having one, more or all the following characteristics:
protein size of 74.455 kDa
expressed both in the soluble and in the insoluble protein fraction after up to 20 hours under anoxic conditions at various temperatures.

In the following further details preferred according to the invention, of a method according to the invention for the production of phloretin are described.

Concerning the provision of a transgenic microorganism (as described herein) it should be stated that basically any method familiar to a person skilled in the art can be used, in order to introduce the nucleic acid sections (a), (a') and (b) described herein or the transgenes described herein into the microorganisms, E. g. basically conjugation, transduction or transformation, in particular by heat-shock treatment, electroporation, conjugation, gene-gun, the lithium-acetate method or transduction. Within the context of the present invention, however, it is generally preferred for the nucleic acid sections (a), (a') and (b) or the transgenes described to be introduced by means of a vector, especially a plasmid vector, in particular a vector according to the invention as described herein (see below). Methods for this are sufficiently known to a person skilled in the art.

A transgenic microorganism within the meaning of the present invention can contain one or more copies of the introduced nucleic acid sections or the transgenes described herein.

Methods allowing, on the basis of the introduced nucleic acid sections or transgenes, an expression of the desired acid sequences or the desired enzyme, are similarly sufficiently known to a person skilled in the art, E. g. using a regulatory element, especially a promoter (see on this point also the attached examples).

As described above in step (ii) of a method according to the invention one or more flavanones and/or one or more precursor(s) or derivative(s) thereof are added to the transgenic microorganism, wherein the transgenic microorganism is cultivated under conditions which allow conversion of the flavanone(s) and/or the precursor(s) or of the derivative or derivative thereof, especially of naringin and/or the precursor or the derivative of naringin, to a dihydrochalcone, especially to phloretin.

As described above in step (ii) of a method according to the invention especially preferably naringin and/or a precursor or a derivative of naringin is added to the transgenic microorganism, wherein the transgenic microorganism is cultivated under conditions which allow conversion of the naringin and/or the precursor or the derivative of naringin to phloretin.

According to a preferred execution of a method according to the invention (as described herein) the (transgenic) microorganisms are initially, that is to say prior to step (ii), cultivated under aerobic conditions, in particular in order to achieve a maximum biomass concentration. In doing so the $OD_{600}$ should preferably be at least in the range 8-15 or above, in particular in the range 5-190, especially in the range 10-180, preferably in the range 15-170. Then the microorganisms in step (ii) are preferably cultivated under anaerobic conditions, wherein the expression of the desired amino acid sequences or the desired enzymes takes place on the basis of the introduced nucleic acid sections or the introduced transgenes, for example stimulated by means of induction by IPTG and/or Lactose (when using a corresponding, suitable promoter or a corresponding, suitable expression system).

Basically it is preferred according to the invention if the incubation in step (ii) takes place at least in part or completely under anaerobic conditions.

Depending on the microorganism a person skilled in the art in step (ii) for the purposes of present invention can create suitable ambient conditions and especially provide a suitable (cultivation). The cultivation preferably takes place in LB or TB medium. Alternatively a (more complex) medium comprising or consisting of plant raw materials, especially from citrus, grapefruit and orange plants, can be used. The cultivation takes place for example at a temperature of more than 20° C., preferably of more than 25° C., especially of more than 30° C. (preferably in the range 30-40° C.), which can especially favour the phloretin formation or increase the yield. Furthermore, an induction temperature (see above) of less than 40° C., especially of less than 35° C. (preferably in the range 20-30° C.), can favour phloretin formation or increase the yield.

Naringin or the precursors or derivatives thereof in relation to the (cultivation) medium, containing the transgenic microorganisms, will be added in step (ii) in particular in a quantity of 0.1 mM-100 mM (mMol/L), preferably of 0.5-95 mM, especially preferably of 1-90 mM, to the transgenic microorganism. Here suitable (co-)solvents can be used.

If for induction (E. g. of the lac operon) one or more suitable inductors, E. g. IPTG or lactose, are used (see above), it is preferred that the inductor in relation to the (cultivation-) medium, containing the transgenic microorganisms, is used in step (ii) in a quantity of 0.001-1 mM, preferably of 0.005-0.9 mM, especially preferably of 0.01-0.8 mM, since in so doing particularly good yields can be achieved.

Concerning the optional isolation and possible purification of phloretin: Here, for example, extractions can be carried out with organic solvents (preferably selected from the following list: isobutane, 2-propanol, toluene, methyl acetate, cyclohexane, 2-butanol, hexane, 1-propanol, light petroleum, 1,1,1,2-tetrafluorethane, methanol, propane, 1-butanol, butane, ethyl methyl ketone, ethyl acetate, diethyl ether, ethanol, dibutyl ether, $CO_2$, tert. butyl methyl ether, acetone, dichloromethane and $N_2O$), especially preferably those which with water develop a visibly discernible phase boundary. Then the removal of the residual water in the solvent and the removal of the solvent itself are possible, followed in turn by re-dissolution of the (for example) phloretin in a (possibly other) solvent, which is suitable for a possible subsequent crystallisation and drying of the product. Alternatively or additionally a purification by adsorption, distillation and/or chromatography can take place.

Further details of the method according to the invention are apparent from the attached examples.

A further aspect of the present invention concerns a transgenic microorganism, containing a nucleic acid section (a), comprising or consisting of a gene coding for a bacterial chalcone isomerase (as the transgene), and/or a nucleic acid section (a'), comprising or consisting of a gene coding for a plant chalcone isomerase (as the transgene), and a nucleic acid section (b), comprising or consisting of a gene coding for a bacterial enoate reductase (as a further transgene).

For the terms employed here, that stated above for these same terms applies by analogy. Preferred microorganisms according to the invention are apparent from the corresponding statements above in connection with a preferred microorganism in the context of the method according to the invention.

The microorganism according to the invention for the purposes of the present invention preferably has at least one chalcone isomerase and one enoate reductase activity, but no phloretin hydrolase activity. The same applies to microorganisms (as described above) to be used by preference in the context of a method according to the invention.

Particularly preferably the microorganism is not a *Eubacterium ramulus*, preferably not a microorganism of the order Clostridiales, more preferably nor not a microorganism of the class Clostridia, especially preferably not a microorganism of the phylum Firmicutes, and is particularly preferably selected from the group comprising facultative anaerobic microorganisms, especially facultative aerobic bacteria, preferably proteobacteria, especially enterobacteria, for example of the genus *Escherichia*, preferably *E. coli*, especially *E. coli* Rosetta, *E. coli* BL21 and *E. coli* SE1, and yeasts, for example *S. cerevesiae* and *P. pastoris*. Otherwise that stated above for microorganisms to be used by preference in the context of a method according to the invention applies by analogy.

Accordingly, a microorganism according to the invention is especially preferred wherein the gene coding for a bacterial chalcone isomerase codes for a chalcone isomerase from a microorganism from the phylum Firmicutes, in particular the class Clostridia, especially the order Clostridiales, especially preferably for a chalcone isomerase from *E. ramulus*, and/or the gene coding for a plant chalcone isomerase codes for a chalcone isomerase from *A. thaliana* or *M. sativa* (for other preferred sources see above), and/or the gene coding for a bacterial enoate reductase codes for an enoate reductase from a microorganism from the phylum Firmicutes, in particular the class Clostridia, especially from the order Clostridiales, especially preferably for an enoate reductase from *E. ramulus*.

It is further preferred if the nucleic acid section (a) comprises or consists of a nucleotide sequence according to SEQ ID NO:1 or a nucleotide sequence with a nucleotide sequence identity of 40% or more for SEQ ID NO:1, in particular of 50% or more, 60% or more or 80% or more, especially preferably of 95% or more, and/or the nucleic acid section (a') comprises or consists of a nucleotide sequence according to SEQ ID NO:6 or SEQ ID NO:7 or a nucleotide sequence with a nucleotide sequence identity of 40% or more for SEQ ID NO:6 or SEQ ID NO:7, in particular of 50% or more, 60% or more or 80% or more, especially preferably of 95% or more, and/or the nucleic acid section (b) comprises or consists of a nucleotide sequence according to SEQ ID NO:2 or SEQ ID NO:5 or a nucleotide sequence with a nucleotide sequence identity of 40% or more for SEQ ID NO:2 or SEQ ID NO:5, in particular of 50% or more, 60% or more or 80% or more, especially preferably of 95% or more.

It is also preferable if the bacterial chalcone isomerase comprises or consists of an amino acid sequence according to SEQ ID NO:3 or an amino acid sequence with an amino acid sequence identity of 40% or more for SEQ ID NO:3, in particular of 50% or more, 60% or more or 80% or more, especially preferably of 95% or more, and/or the plant chalcone isomerase comprises or consists of an amino acid sequence according to SEQ ID NO:8 or SEQ ID NO:9 or an amino acid sequence with an amino acid sequence identity of 40% or more for SEQ ID NO:8 or SEQ ID NO:9, in particular of 50% or more, 60% or more or 80% or more, especially preferably of 95% or more, and/or the bacterial enoate reductase comprises or consists of an amino acid sequence according to SEQ ID NO:4 or an amino acid sequence with an amino acid sequence identity of 40% or more for SEQ ID NO:4, in particular of 50% or more, 60% or more or 80% or more, especially preferably of 95% or more.

For the determination of the nucleotide sequence and amino acid sequence identity that stated above applies here by analogy.

A further aspect of the present invention concerns a vector, E. g. a transport vesicle ("gene shuttle") for transfer of external nucleic acid(s) into a receiver cell, especially a plasmid vector, allowing the cloning of one or more nucleic acid sections, containing a nucleic acid section (a), comprising or consisting of a gene coding for a bacterial chalcone isomerase, and/or a nucleic acid section (a'), comprising or consisting of a gene coding for a plant chalcone isomerase, and/or a nucleic acid section (b), comprising or consisting of a gene coding for a bacterial enoate reductase. Here it is preferred if the vector contains both a nucleic acid section (a) and/or (a'), as well as a nucleic acid section (b).

Apart from nucleic acid section(s) (a), (a') and/or (b) a vector according to the invention may contain for the purposes of the present invention further normal components, especially those which improve or possibly actually allow the expression of the transgenes described herein in microorganisms, especially in those as described above. Basically a vector according to the invention preferably also contains one or more further components or elements selected from the group consisting of promoter, sequence of origin, sequence for affinity chromatography purification, selection marker, operator sequence, terminator, ribosomal binding sites, protease cleavage sequence, recombination binding sites, sequences of fusion proteins and chaperone sequences.

With the vectors according to the invention (as described above) it is also preferred if the gene coding for a bacterial chalcone codes for a chalcone isomerase from a microorganism from the phylum Firmicutes, in particular the class Clostridia, especially the order Clostridiales, especially preferably for a chalcone isomerase from *E. ramulus*, and/or the gene coding for a plant chalcone isomerase codes for a chalcone isomerase from *A. thaliana* or *M. sativa* (for other preferred sources see above), and/or the gene coding for a bacterial enoate reductase codes for an enoate reductase from a microorganism from the phylum Firmicutes, in particular the class Clostridia, especially the order Clostridiales, especially preferably for an enoate reductase from *E. ramulus*.

It is especially preferable if the nucleic acid section (a) comprises or consists of a nucleotide sequence according to SEQ ID NO:1 or a nucleotide sequence with a nucleotide sequence identity of 40% or more for SEQ ID NO:1, in particular of 50% or more, 60% or more or 80% or more, especially preferably of 95% or more, and/or the nucleic acid section (a') comprises or consists of nucleotide sequence according to SEQ ID NO:6 or SEQ ID NO:7 or a nucleotide sequence with a nucleotide sequence identity of 40% or more for SEQ ID NO:6 or SEQ ID NO:7, in particular of 50% or more, 60% or more or 80% or more, especially preferably of 95% or more, and/or the nucleic acid section (b) comprises or consists of a nucleotide sequence according to SEQ ID NO:2 or SEQ ID NO:5 or a nucleotide sequence with a nucleotide sequence identity of 40% or more for SEQ ID NO:2 or SEQ ID NO:5, in particular of 50% or more, 60% or more or 80% or more, especially preferably of 95% or more.

It is further preferable if the bacterial chalcone isomerase comprises or consists of an amino acid sequence according to SEQ ID NO:3 or an amino acid sequence with an amino acid sequence identity of 40% or more for SEQ ID NO:3, in particular of 50% or more, 60% or more or 80% or more, especially preferably of 95% or more, and/or the plant chalcone isomerase comprises or consists of an amino acid sequence according to SEQ ID NO:8 or SEQ ID NO:9 or an amino acid sequence with an amino acid sequence identity of 40% or more for SEQ ID NO:8 or SEQ ID NO:9, in particular of 50% or more, 60% or more or 80% or more, especially preferably of 95% or more, and/or the bacterial enoate reductase comprises or consists of an amino acid sequence according to SEQ ID NO:4 or an amino acid sequence with an amino acid sequence identity of 40% or more for SEQ ID NO:4, in particular of 50% or more, 60% or more or 80% or more, especially preferably of 95% or more.

Here again, for the determination of the nucleotide sequence and amino acid sequence identity that stated above applies by analogy.

Figure 2:
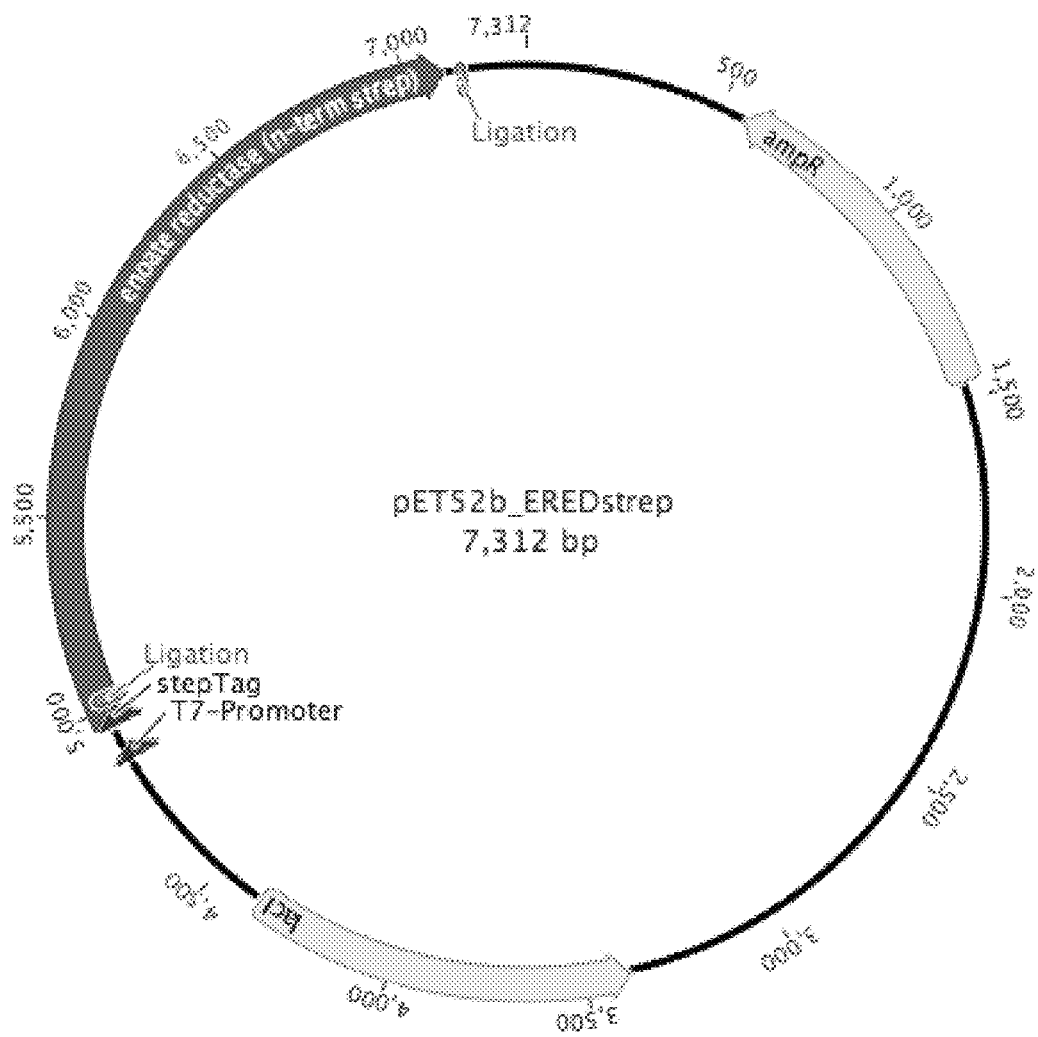
FIG. 2: Plasmid pET28b_CHI for heterologous expression and characterization of the CHI from *E. ramulus* DSM 16296.
Figure 3:
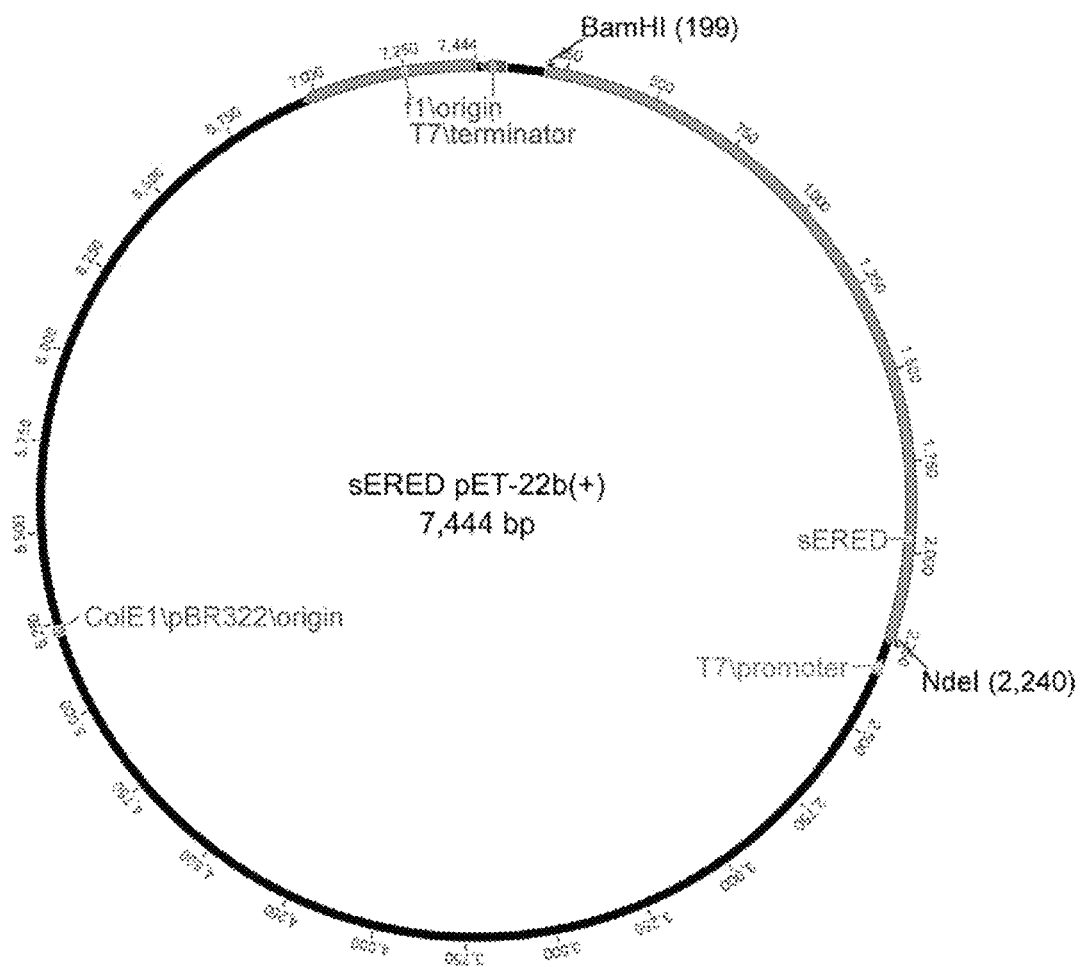
FIG. 3: Plasmid pET22b_ERED for heterologous expression and characterization of the ERED from *E. ramulus* DSM 16296.
Figure 4:
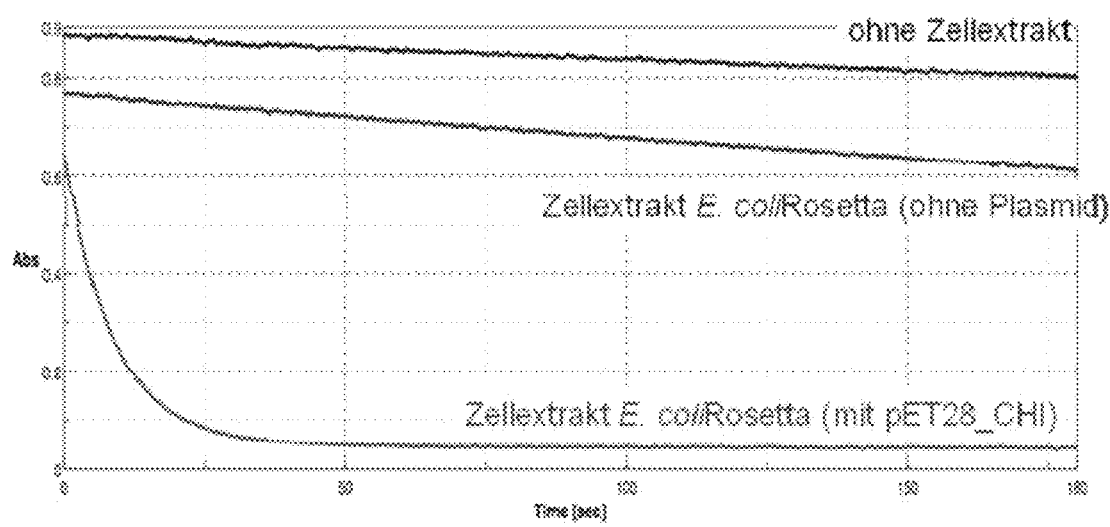
FIG. 4 is a graph showing lines representing without cell extract, with cell extract *E. coli* Rosetta (without plasmid), and with cell extract *E. coli* Rosetta (with pET28_HI)

Especially preferred, and for the purposes of the invention especially suitable, vectors and components or elements thereof are apparent from the attached examples and figures (FIG. 1: Plasmid pET52b_EREDstrep for heterologous expression and characterization of the ERED from *E. ramulus* DSM 16296; FIG. 2: Plasmid pET28b_CHI for heterologous expression and characterization of the CHI from *E. ramulus* DSM 16296; FIG. 3: Plasmid pET22b_ERED for heterologous expression and characterization of the ERED from *E. ramulus* DSM 16296).

The present invention also concerns a host cell, containing one or more identical or different vectors according to the invention as described herein. Preference according to the invention is for a host cell, which contains both one or more vectors with a nucleic acid section (a), comprising or consisting of a gene coding for a bacterial chalcone isomerase, and/or a nucleic acid section (a'), comprising or consisting of a gene coding for a plant chalcone isomerase, and also one or more vectors with a nucleic acid section (b), comprising or consisting of a gene coding for a bacterial enoate reductase. Especially preferred is a host cell, containing one or more vectors with both a nucleic acid section (a) and/or (a'), and a nucleic acid section (b).

With a host cell according to the invention it is in particular a case of a microorganism (as described above) according to or to be used according to the invention. The host cells or microorganisms according to or to be used according to the invention described herein are or in particular serve as a (production) strain for biotechnological production of the dihydrochalcones described herein, especially of phloretin (as described above).

In the following the present invention is explained in more detail using examples, wherein these do not restrict the subject-matter of the attached claims.

EXAMPLE 1

Provision of Transgenic Microorganisms (See Step (i))

1.1 CHI:

Using the identified gene sequence of the chalcone isomerase from *E. ramulus* two primers were prepared, which were used for reproduction of the genomic DNA by means of PCR. Here, with the help of the primers, in front of the gene a restriction interface was attached for Kpn1 and BamH1 and behind the gene an interface for Not1 to the target sequence, which were used for ligation of the gene section in the target vector.

Primers used (sequence sections, binding directly to the gene are shown in italics):

```
forward:
CTAATCGGATCCGGTACC*ATGGCAGATTTCAAATTCGAACCAATG* reverse:
TCAGTAGCGGCCGC*TTATCTCATGGTGATGTATCCACGATAATT*
```

The resultant DNA fragment of the chalcone isomerase gene was inserted by means of TOPO TA Cloning® (from Invitrogen, Carlsbad, Calif., USA) in the vector pCR®2.1-TOPO®. Following successful transformation of this construct the chalcone isomerase gene was cut out from this vector via Nco1 and Not1 and inserted in the target vector pET28b likewise cut with Nco1 and Not1. The plasmid was introduced into *E. coli* Rosetta and successfully expressed there.

Following successful transformation the sequence identity was confirmed by means of sequencing.

1.2 ERED:

The enoate reductase was amplified with the following specific primers from the genomic DNA (sequence sections binding directly to the gene are shown in italics):

```
forward:
GATCCTCGAGA*TGGCAGAAAAAAATCAGTATTTTCCACA* reverse:
GATCAAGCTT*AGATAATTTCCATTGCTGCGGTCCA*
```

Here in front of the gene an interface for SacI was inserted and behind the gene an interface for HindIII, in order to allow subsequent cloning.

This fragment was also processed further with the TOPO TA Cloning®-Kit. The sequence identity of the resultant clone (with vector pCR®2.1-TOPO® and gene for enoate reductase contained therein) was confirmed by means of sequencing.

The gene from this plasmid was amplified with primers, which inserted a Kpn1 interface in front of the gene (sequence sections binding directly to the gene are shown in italics; the Kpn1 interface inserted in the forward primer (containing no sequence sections binding directly to the gene) were marked in bold):

```
forward:
AGTGTGATGGGTACCTGCAGAATTCGCC reverse:
GATCAAGCTTAGATAATTTCCATTGCTGCGGTCCA
(see above)
```

The vector pCR®2.1-TOPO® similarly contains a SacI interface, which was used from further cloning.

Following the PCR this PCR product was digested with Sac1 and Kpn1 and then the ligation in the plasmid pET52b similarly digested with Sac1 and Kpn1. The gene construct was expressed in *E. coli* Rosetta.

Sequencing was used to confirm that the gene of the enoate reductase was successfully ligated in the plasmid pET52b, wherein the inserted N-terminal strep tag remained available, allowing a highly specific protein purification.

In the context of a further approach a codon-optimised sequence with the interfaces Nde1 and BamH1 was ligated in the vector pET-22b and expressed in *E. coli* BL21.

1.3 Antibiotic-free expression:

Furthermore, the gene sections of the CHI can be integrated via the interfaces BamH1 and XHO1 in the plasmid pET22b with the synthetic ERED gene.

For this the CHI gene is amplified via a PCR with the forward-primer GTCTAGGATCCAGAAATAATTTTGTTTAACTTTAAGAAGGAGA and the pET-rP-primer CTAGTTATTGCTCAGCGG, wherein the Xba1 interface before the CHI gene is mutated via the forward-primer into a BamHI interface. Then the construct from both genes is cut via the interfaces Xba1 and Xho1 from the plasmid and ligated in the plasmid pStaby1.2 prepared with Xba1 and Xho1.

Then an antibiotic-free expression can take place by means of the StabyExpress-system.

EXAMPLE 2

Biotechnological Production of Phloretin (See Step (ii))

TB medium comprising 24 g yeast extract, 12 g Tryptone and 4 g glycerine is made up to 900 ml and autoclaved at 121° C. for 15 minutes. A separately prepared saline solution (0.72 M of $K_2HPO_4$ and 0.17 M of $KH_2PO_4$) is autoclaved under the same conditions. Then 100 ml of the saline solution is added to 900 ml of the sterile TB medium. LB medium comprising 5 g yeast extract, 10 g Tryptone and 10 g NaCl is made up to 1000 ml with distilled water and autoclaved for 15 minutes at 121° C.

The *E. coli* Rosetta or *E. coli* BL21 (see above) transformed for example according to Example 1 are first cultivated in 250 ml Erlenmeyer flasks (with baffles), filled with 50 ml LB medium, for approximately 8 hours at 37° C. and 180 rpm. From this culture 7 ml are then taken and used to inoculate a mini fermenter containing 700 ml of TB medium (as described above). The culture is grown over night at 25° C. and 150-200 rpm with 40% oxygen saturation to achieve a maximum biomass concentration.

Before (over)expression of the introduced nucleic acid sections or the introduced transgene the air supply is terminated and the existing oxygen is driven out by nitrogen.

To induce (over)expression initially an IPTG concentration of 1 mM in the medium is set and then 7 ml of a naringenin solution (100 mM in DMSO) added.

Further cultivation then takes place in the expression phase for at least 8-20 hours under anoxic conditions.

EXAMPLE 3

Characterisation of the Expressed CHI

Following expression of for example pET28b_CHI in *E. coli* (see above) CHI can be established both in the soluble and in the insoluble fractions.

Figure 5:
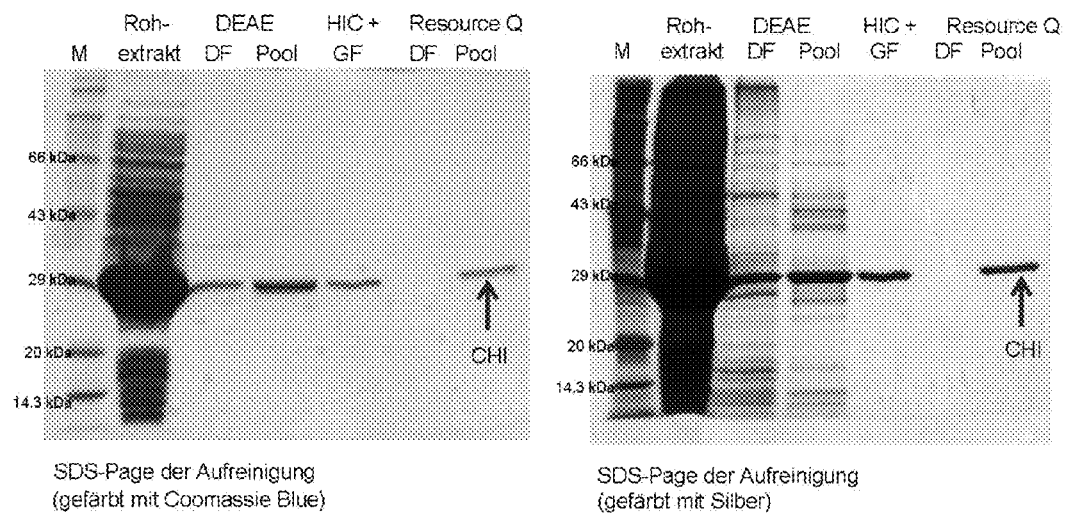
FIG. 5 provides examples of the results of the individual purification steps following expression of the vector pET28b_CHI in *E. coli*.

Following purification with for example anion exchange chromatography, hydrophobic interaction chromatography, size exclusion chromatography and/or Resource Q purification the CHI can be isolated for characterization (FIG. 5 provides examples of the results of the individual purification steps following expression of the vector pET28b_CHI in *E. coli*).

Our own investigations produced the results shown in Table 4:

TABLE 4

Characterisation of the enzyme activity of the CHI following expression of the vector pET28b_CHI in *E. coli*

| KM [µmol/l] | Vmax [U/mg] | kcat [s−1] | kcat/KM [l * mol−1 * s−1] |
|---|---|---|---|
| 36.83 | 107.3 | 416.7 | 1.13 * 107 |

EXAMPLE 4

(Further) Characterization of the Expressed Enzymes CHI and ERED

Tables 5-6 show (further) results of the characterization of the expressed enzymes CHI and ERED (from *E. ramulus* DSM 16296 during anaerobic conversion (see above)).

TABLE 5

Anaerobic cultivation

| Time in h | Naringenin in mM | Phloretin in mM |
|---|---|---|
| 0.25 | 1.00 | 0.09 |
| 1.75 | 0.77 | 0.44 |
| 3.25 | 0.59 | 0.62 |
| 4.75 | 0.45 | 0.68 |
| 6.25 | 0.44 | 0.68 |
| 10.25 | 0.42 | 0.74 |
| 21.00 | 0.29 | 0.70 |
| 26.00 | 0.27 | 0.71 |

TABLE 6

Anaerobic fermentation with CHI and ERED; 10 mM naringenin

| Time in hours | Phloretin in mM |
|---|---|
| .00 | 0.008 |
| 1.00 | 0.189 |
| 2.00 | 0.282 |
| 3.00 | 0.404 |
| 4.00 | 0.485 |
| 5.00 | 0.494 |
| 6.00 | 0.694 |
| 10.00 | 0.821 |
| 22.00 | 0.855 |
| 26.00 | 0.840 |

The enzymes CHI and ERED (from *E. ramulus* DSM 16296) were placed separately for expression in a vector system suitable for *E. coli* (see above). Then the activity of these—following addition of naringenin in a defined culture medium—could be determined by means of HPLC.

The values in Table 5 show the formation as a function of time of phloretin (with a reduction in the naringenin concentration), pointing to the activity of the enzymes CHI and ERED.

The values in the table in Table 6 show (further) results of the chalcone isomerase activity of the expressed CHI, obtained by photometric determination (at 368 nm) in relation to the degradation of naringenin chalcone (to form phloretin).

A photometric determination allowed—for further investigation of the CHI activity—the reduction over time in the concentration of naringenin chalcone in a cell-free protein crude extract to be observed. A control experiment (plasmid without CHI) showed a reduction in the naringin chalcone used as the marker substance.

EXAMPLE 5

Results of (Comparative) Expression Experiments with *E. ramulus*

*E. ramulus* (DSMZ 16296) was cultivated anaerobically according to Herles et al. (Arch Microbiol (2004) 181: 428-434) in ST medium. For its preparation 9 g of tryptically treated meat peptone, 1 g peptone, 3 g meat extract, 4 g yeast extract, 6 g glucose, 3 g sodium chloride, 2 g disodium hydrogen phosphate, 0.5 ml Tween 80, 0.25 g cystine, 0.25 g cysteine-HCl, 0.1 g magnesium sulphate heptahydrate, 5 mg iron sulphate heptahydrate and 3.4 mg manganese sulphate dehydrate were adjusted to pH 7.0, made up to 1 l with distilled water and then autoclaved at 121° C. for 15 minutes.

Cultivations were performed both in a conventional steel reactor with stirrer, and in bag reactors with Wipp system under anoxic conditions, wherein the temperature was maintained at 37° C. and the pH at 7.0 with acid and alkaline solution (HCl or NaOH).

Figure 6:
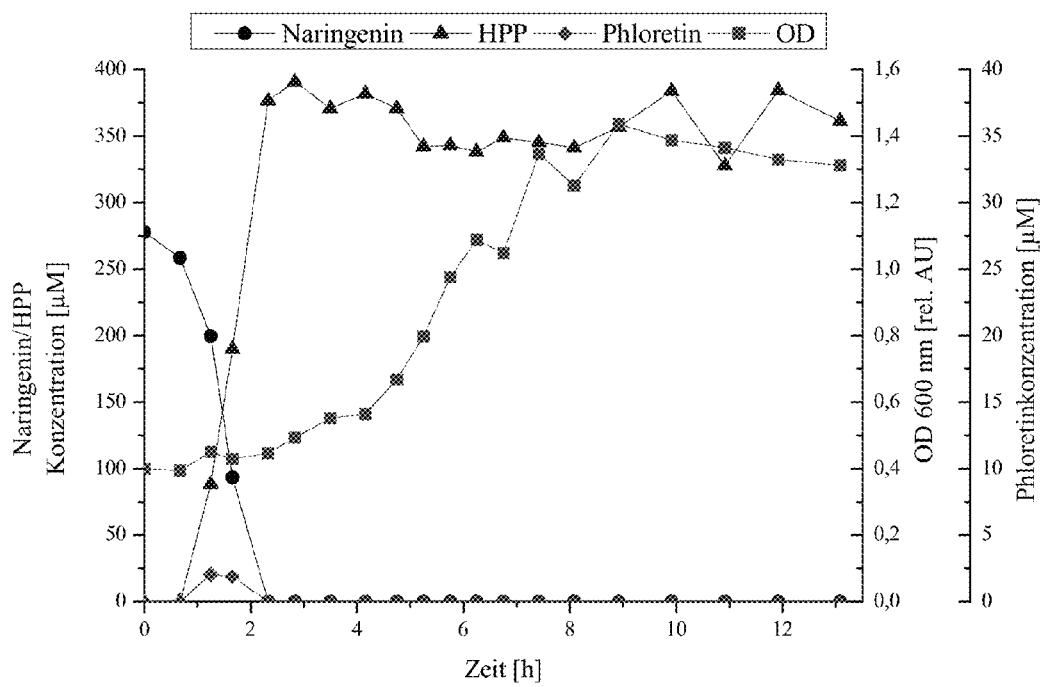
FIG. 6 is a graph of Naringenin/HPP/Concentration [µM] against Phloretin concentration [µM] over time [h].

In an example fermentation at the start of cultivation 275 µM naringenin were added to the medium and the growth and the conversion of the substrate determined (for results see FIG. 6).

SEQ ID NO: 1
ATGGCAGATTTCAAATTCGAACCAATGAGAAGTCTTATCTACGTTGACTGCGTAAGC

GAAGACTACAGACCAAAACTTCAGAGATGGATTTATAAAGTACATATTCCGGACAG

-continued

CATCTCTCAGTTTGAGCCGTATGTTACCAAATATGCATTTTATCCGTCCTTCCCGATT
CCACCACAGGGTGATCGTTTCGGATACGCAAGAATGCAGCTGACAGAGCATCACTG
GTTAGTAAGCGACCTTGATCCTCGTCTTGAGATCAAAGCAATCGCTGAGACATTCCC
GATGGACGTACTTGTATGGCAGGGACAGATCCCGGCAGCAGCTCATACAGACGCTC
AGATCGATTCTGACGGAGATGCAGGAAATGCAGCCCGTAAATCCAACAATGCAGAA
GGAAATCCATTTATCTTTGCATTCCTTCCGATGTGGTGGGAGAAAGACCTGAAAGGA
AAAGGACGTACGATCGAGGACGGCGCAAACTATCGTTTCAATATGACTATCGGTTTC
CCAGAAGGCGTAGACAAAGCAGAGGGAGAGAAATGGTTATTTGAGAAAGTAGTTCC
GATTCTTCAGGCAGCTCCGGAGTGTACACGTGTACTTGCAAGTGCCGTAAAGAAAG
ACATCAACGGATGCGTAATGGATTGGGTACTTGAAATCTGGTTTGAGAATCAGTCCG
GATGGTACAAAGTAATGGTAGATGACATGAAAGCACTTGAAAAACCGTCATGGGCT
CAGCAGGATGCTTTCCCGTTCCTGAAACCATACCACAATGTTTGCAGTGCAGCAGTT
GCTGATTATACACCAAGCAACAACCTTGCAAATTATCGTGGATACATCACCATGAGA
TAA

SEQ ID NO: 2
ATGGCAGAAAAAAATCAGTATTTTCCACATTTGTTTGAGCCGTTAAAAGTTGGTTCA
AAGACAATTAAGAACCGTATTGAGGCAGCACCGGCTTTATTTGCATTCGAGCATTAT
ATCGAACTGAATCCGGATCCGTTTGGCTATACCACACCGGTTCCGGAGCGTGCGTTC
CGTATGCTGGAGGCAAAGGCAAAAGGAGGGGCAGGAATTGTATGTCTGGGTGAGTT
AAGCCCGAATCATGAGTATGACAAACGGTTTCCGTTTGAACCGTATCTTGATTTTAC
ATCCAGATCAGATAAGCAGTTTGAAATTATGAAGGAAACTGCGGAGATGATCAAAA
GCTATGGGGCATTTCCGATGGGCGAGCTGCTTTCCTGCGGTGAAATCAAGACAAATA
TCGGAGATGGTATCAATCCGAAGGGACCATCTGAGAAAGATCTTCCGGATGGCTCTC
ATGTGGAGGCGTTTACAAAAGAAGAGATTTTAAGCTGCTATCAGGATTATGTAACTG
CATGTAAATGGTTTCAGGCAGCAGGCTGGGAAGGCATTATGATCCACTGCGGACAT
GGCTGGCTTCCGGCACAGTTCCTGTCTCCGCAATACAATAAACGTACCGATGAGTAT
GGTGGATCTTTTGAAAACAGAGCAAGATTTACTGTTGATCTGTTAAAAACTGTTCGT
GAAGCTATGGGACCGGACTTCGTGATCGAGATCCGTGTCAGCAGCTCTGAGCATTTA
CCGGGCGGATTAGAGCTGGAAGATGCTGTAAATTATTGTAAACTGTGTGAGCCATAC
ATTGATATGATCCATGTCTCCTGTGGTCATTACCTGAGTTCTTCCAGAAGTTGGGAGT
TCACAACTGCTTATGCACCGCATGGTCCGAATATTGAACCGGCAGCTGTTATCAAAC
AGAACGTATCCATTCCGGTTGCGGCAGTCGGCGGCATCAATTCTCCGGAACAGGCG
GAAGAGGCAATCGCGTCAGGAAAAATCGATATGGTATCCATGGGACGTCAGTTCTT
TGCAGATCCGGCATTTCCAAACAAGGCAAAAGAAGGGCATGCAGATGAGATCCGTC
GCTGTCTCGCGCTGCGGAAGATGCTATCCGGGTCCGTCCGGCGAGCATGAAACAGAG
ATCTGGACGGTGAAATTCCCACCACTGGATTCCTGTACCATCAATCCATATGATGTA
TGGCCGGCATCTCATCATAAAGTCCTTCCGGACCGCATGCCGAAACCGGAAGCAAG
CCGTAAGGTATTGGTAGTAGGCGGCGGCTGTGGCGGTCTGCAGACAGCGATCACAG
CATCAGACAGAGGTCATCAGGTAATCCTGTGCGAAAAATCCGGAGTATTAGGCGGT
CTGATCAATTTTACGGATCATACGGATCATAAAGTAGATATCAGAAACTTCAAAGAT
CTGCTGATCCGCGATGTGGAGAAACGTCCGATCGAAGTAAGATTAAACTGTGAAGT

-continued

```
AACACCGGAACTCATCAGAGAAATTGCTCCGGAAGCAGTTGTACTGGCCGTCGGAT

CCGATGATCTGATCCTTCCAATCGAGGGAATTGAAAATGCGGTAACAGCAATGGAC

GTATACAGCAATGACTTTGCAGGTCTTGGAAAGAGCACCATCGTACTCGGTGGCGGT

CTGGTTGGCTGTGAGGCAGCCGCAGATTATATTGATCACGGTGTAGAGACAACGATT

GTTGAAATGAAAGGTGCGCTGATGCCGGAGACAACCGGTCTGTACCGTACAGCTGT

ACATGATTTCATCGACAAAAACGGCGGCAAATACGAAGTAAATGCAAAAGTTGTCA

AAGTTGGCAAAGATTTTGTGGTAGCGGAACAAGATGGGAAAGAGATTACCATCAAA

GCAGATTCTGTTGTCAATGCAATGGGACGCCGTGCGCATGCGACAGAAGCACTTGA

GACAGCTATCAAAGAAGCTGGTATTCCGGTATGGAAGATCGGTGACTGTGTCCGTGC

GCGTCAGATCGGTGATGCGGTAAGAGAAGGCTGGACCGCAGCAATGGAAATTATCT

AA
```

SEQ ID NO: 4
```
MAEKNQYFPHLFEPLKVGSKTIKNRIEAAPALFAFEHYIELNPDPFGYTTPVPERAFRML

EAKAKGGAGIVCLGELSPNHEYDKRFPFEPYLDFTSRSDKQFEIMKETAEMIKSYGAFP

MGELLSCGEIKTNIGDINPKGPSEKDLPDGSHVEAFTKEEILSCYQDYVTACKWFQAA

GWEGIMIHCGHGWLPAQFLSPQYNKRTDEYGGSFENRARFTVDLLKTVREAMGPDFVI

EIRVSSSEHLPGGLELEDAVNYCKLCEPYIDMIHVSCGHYLSSSRSWEFTTAYAPHGPNIE

PAAVIKQNVSIPVAAVGGINSPEQAEEAIASGKIDMVSMGRQFFADPAFPNKAKEGHAD

EIRRCLRCGRCYPGPSGEHETEIWTVKFPPLDSCTINPYDVWPASHHKVLPDRMPKPEAS

RKVLVVGGGCGGLQTAITASDRGHQVILCEKSGVLGGLINFTDHTDHKVDIRNFKDLLI

RDVEKRPIEVRLNCEVTPELIREIAPEAVVLAVGSDDLILPIEGIENAVTAMDVYSNDFAG

LGKSTIVLGGGLVGCEAAADYIDHGVETTIVEMKGALMPETTGLYRTAVHDFIDKNGG

KYEVNAKVVKVGKDFVVAEQDGKEITIKADSVVNAMGRRAHATEALETAIKEAGIPVW

KIGDCVRARQIGDAVREGWTAAMEII
```

SEQ ID NO: 3
```
MADFKFEPMRSLIYVDCVSEDYRPKLQRWIYKVHIPDSISQFEPYVTKYAFYPSFPIPPQG

DRFGYARMQLTEHHWLVSDLDPRLEIKAIAETFPMDVLVWQGQIPAAAHTDAQIDSDG

DAGNAARKSNNAEGNPFIFAFLPMWWEKDLKGKGRTIEDGANYRFNMTIGFPEGVDKA

EGEKWLFEKVVPILQAAPECTRVLASAVKKDINGCVMDWVLEIWFENQSGWYKVMVD

DMKALEKPSWAQQDAFPFLKPYHNVCSAAVADYTPSNNLANYRGYITMR
```

SEQ ID NO: 5
Codon-optimised nucleotide sequence for expression of the ERED in E. coli BL21, integrated in pET 22b, was cloned with NdeI and BamH1:
```
ATGGCAGAAAAGAACCAATACTTCCCGCACCTGTTTGAACCGCTGAAAGTCGGCTCT

AAAACCATTAAAAATCGCATCGAAGCAGCACCGGCCCTGTTTGCATTCGAACATTAT

ATCGAACTGAACCCGGACCCGTTTGGTTACACCACGCCGGTGCCGGAACGTGCATTC

CGTATGCTGGAAGCCAAAGCAAAGGCGGTGCCGGCATTGTTTGTCTGGGTGAACT

GAGCCCGAATCACGAATATGATAAACGCTTTCCGTTCGAACCGTACCTGGATTTTAC

CAGCCGTTCTGACAAACAGTTCGAAATTATGAAAGAAACGGCAGAAATGATCAAA

GCTATGGCGCTTTTCCGATGGGTGAACTGCTGTCGTGCGGTGAAATCAAAACCAACA

TTGGCGATGGTATCAATCCGAAAGGCCCGTCAGAAAAAGATCTGCCGGACGGTTCG

CATGTGGAAGCCTTCACCAAAGAAGAAATCCTGTCATGTTACCAGGATTACGTTACG
```

-continued

```
GCATGCAAATGGTTCCAAGCGGCCGGCTGGGAAGGTATTATGATCCATTGTGGCCAC

GGTTGGCTGCCGGCGCAGTTTCTGAGCCCGCAATATAACAAACGCACCGATGAATA

CGGCGGTTCTTTTGAAAATCGTGCGCGCTTCACCGTCGATCTGCTGAAAACGGTGCG

TGAAGCGATGGGCCCGGACTTCGTGATTGAAATCCGTGTTAGCTCTAGTGAACATCT

GCCGGGCGGTCTGGAACTGGAAGATGCGGTGAACTATTGCAAACTGTGTGAACCGT

ACATTGACATGATCCATGTTAGTTGCGGCCACTATCTGTCCTCATCGCGCTCCTGGG

AATTTACCACGGCTTACGCGCCGCACGGTCCGAACATCGAACCGGCAGCTGTCATTA

AACAGAATGTGAGCATCCCGGTTGCAGCAGTCGGCGGTATCAACTCTCCGGAACAA

GCGGAAGAAGCCATTGCAAGTGGCAAAATCGATATGGTTAGCATGGGCCGTCAGTT

TTTCGCTGACCCGGCGTTTCCGAATAAAGCAAAAGAAGGCCATGCTGATGAAATTCG

TCGCTGCCTGCGTTGTGGTCGCTGCTATCCGGGCCCGAGTGGTGAACACGAAACCGA

AATCTGGACGGTGAAATTCCCGCCGCTGGATAGTTGTACCATTAACCCGTACGACGT

GTGGCCGGCATCCCATCACAAAGTTCTGCCGGATCGCATGCCGAAACCGGAAGCGT

CCCGTAAAGTTCTGGTGGTTGGCGGTGGCTGTGGTGGTCTGCAGACCGCAATCACGG

CATCAGACCGCGGCCATCAAGTCATTCTGTGCGAAAAATCGGGTGTGCTGGGTGGCC

TGATTAACTTTACCGATCATACGGACCACAAAGTTGATATTCGCAATTTCAAAGATC

TGCTGATCCGTGACGTCGAAAAACGCCCGATTGAAGTTCGTCTGAATTGTGAAGTCA

CCCCGGAACTGATTCGTGAAATCGCTCCGGAAGCAGTCGTGCTGGCAGTGGGCAGT

GATGACCTGATTCTGCCGATCGAAGGTATTGAAAACGCCGTTACCGCAATGGATGTC

TATAGCAATGACTTTGCCGGCCTGGGTAAATCTACGATCGTGCTGGGTGGCGGTCTG

GTTGGCTGCGAAGCAGCTGCGGATTATATCGATCATGGCGTGGAAACCACGATTGTT

GAAATGAAAGGCGCACTGATGCCGGAAACCACGGGTCTGTATCGTACCGCTGTGCA

CGATTTTATTGACAAAAACGGCGGTAAATACGAAGTCAATGCCAAAGTTGTCAAAG

TGGGCAAAGATTTCGTGGTTGCAGAACAGGACGGTAAAGAAATTACCATCAAAGCG

GATTCTGTCGTGAATGCGATGGGCCGTCGCGCTCACGCAACCGAAGCTCTGGAAAC

GGCGATTAAAGAAGCCGGCATCCCGGTTTGGAAAATTGGTGATTGCGTCCGTGCCCG

CCAAATCGGTGACGCAGTTCGTGAAGGCTGGACGGCTGCAATGGAAATCATCTAA
```

SEQ ID NO: 6

```
ATGGCTGCATCAATCACCGCAATCACTGTGGAGAACCTTGAATACCCAGCGGTGGTT

ACCTCTCCGGTCACCGGCAAATCATATTTCCTCGGTGGCGCTGGGGAGAGAGGATTG

ACCATTGAAGGAAACTTCATCAAGTTCACTGCCATAGGTGTTTATTTGGAAGATATA

GCAGTGGCTTCACTAGCTGCCAAATGGAAGGGTAAATCATCTGAAGAGTTACTTGA

GACCCTTGACTTTTACAGAGACATCATCTCAGGTCCCTTTGAAAAGTTAATTAGAGG

GTCAAAGATTAGGGAATTGAGTGGTCCTGAGTACTCAAGGAAGGTTATGGAGAACT

GTGTGGCACACTTGAAATCAGTTGGAACTTATGGAGATGCAGAAGCTGAAGCTATG

CAAAAATTTGCTGAAGCTTTCAAGCCTGTTAATTTTCCACCTGGTGCCTCTGTTTTCT

ACAGGCAATCACCTGATGGAATATTAGGGCTTAGTTTCTCTCCGGATACAAGTATAC

CAGAAAAGGAGGCTGCACTCATAGAGAACAAGGCAGTTTCATCAGCAGTGTTGGAG

ACTATGATCGGCGAGCACGCTGTTTCCCCTGATCTTAAGCGCTGTTTAGCTGCAAGA

TTACCTGCGTTGTTGAACGAGGGTGCTTTCAAGATTGGAAACTGATGATGATTATAC

TCCTATATCACTGCATTTCCAAAAGCGTTGCAGCACAAGAATGAGACCATGAACTTT
```

-continued

TTTAAGTCTACACGTTTAATTTTTTGTATATCTATTTACCTTCTTATTAGTATCAATAA

TATGAAATGAAAGATCTTGCTTTCTACTCTTGTACTATTTCTGTGATAGATAATGTTA

ATGAGTATCTTCATCAATAAAAGTGATTTGTTTTGTTTGTTC

SEQ ID NO: 7

ATGTCTTCATCCAACGCCTGCGCCTCTCCGTCACCGTTCCCGCCGTCACGAAGCTTC

ATGTAGACTCCGTCACGTTTGTACCGTCCGTCAAGTCACCGGCCTCCTCCAATCCATT

ATTCCTCGGCGGCGCCGGTGTCCGAGGCCTTGATATCCAAGGTAAATTCGTGATCTT

CACCGTCATTGGAGTATACCTAGAGGGTAACGCCGTTCCTTCTCTATCTGTCAAGTG

GAAGGGAAAAACTACGGAGGAGCTAACAGAATCTATCCCGTTCTTCCGTGAAATAG

TCACCGGTGCGTTTGAGAAGTTTATCAAGGTGACAATGAAACTGCCGTTAACGGGAC

AACAATATTCGGAGAAAGTGACGGAGAATTGTGTGGCTATATGGAAACAATTAGGG

CTTTATACGGACTGTGAAGCTAAAGCTGTGGAGAAGTTCTTGGAGATCTTCAAGGAA

GAAACATTCCCTCCCGGTTCATCGATCCTCTTCGCTCTCTCCCCTACCGGCTCTCTTA

CGGTTGCGTTTTCGAAAGATGATAGTATCCCTGAAACCGGGATCGCTGTGATCGAGA

ACAAATTGTTGGCGGAGGCGGTTCTGGAATCTATCATCGGGAAGAACGGTGTGTCA

CCTGGCACTAGGTTAAGTGTTGCAGAAAGATTATCTCAGCTAATGATGAAGAACAA

GGACGAAAAGGAAGTTAGTGATCACTCTGTTGAGGAAAAACTAGCCAAAGAGAACT

GAGAATGATAGATTTTTCTTGTGTTT

SEQ ID NO: 8

MAASITAITVENLEYPAVVTSPVTGKSYFLGGAGERGLTIEGNFIKFTAIGVYLEDIAVAS

LAAKWKGKSSEELLETLDFYRDIISGPFEKLIRGSKIRELSGPEYSRKVMENCVAHLKSV

GTYGDAEAEAMQKFAEAFKPVNFPPGASVFYRQSPDGILGLSFSPDTSIPEKEAALIENK

AVSSAVLETMIGEHAVSPDLKRCLAARLPALLNEGAFKIGN

SEQ ID NO: 9

MSSSNACASPSPFPAVTKLHVDSVTFVPSVKSPASSNPLFLGGAGVRGLDIQGKFVIFTVI

GVYLEGNAVPSLSVKWKGKTTEELTESIPFFREIVTGAFEKFIKVTMKLPLTGQQYSEKV

TENCVAIWKQLGLYTDCEAKAVEKFLEIFKEETFPPGSSILFALSPTGSLTVAFSKDDSIPE

TGIAVIENKLLAEAVLESIIGKNGVSPGTRLSVAERLSQLMMKNKDEKEVSDHSVEEKLA

KEN

What is claimed is:

1. A transgenic microorganism containing transgenes, said transgenes comprising
a nucleic acid section (a), comprising a gene coding for a bacterial chalcone isomerase, or
a nucleic acid section (a'), comprising a gene coding for a plant chalcone isomerase, or both nucleic acid section (a) and nucleic acid section (a');
and
a nucleic acid section (b), comprising a gene coding for an enoate reductase from *E. ramulus* operative to form a dihydrochalcone as a product.

2. The microorganism according to claim 1, wherein the microorganism has chalcone isomerase and enoate reductase activity, but no phloretin hydrolase activity.

3. The microorganism according to claim 1, wherein the microorganism is not a microorganism of the phylum Firmicutes.

4. Microorganism according to claim 3, wherein the microorganism is not *Eubacterium ramulus*.

5. The microorganism according to claim 1, wherein the microorganism is selected from the group consisting of facultative anaerobic microorganisms.

6. The microorganism according to claim 5, wherein the microorganism is selected from the group consisting of enterobacteria and yeasts.

7. The microorganism according to claim 1, wherein
the gene coding for a bacterial chalcone isomerase codes for a chalcone isomerase from *E. ramulus*, or
the gene coding for a plant chalcone isomerase codes for a chalcone isomerase from *A. thaliana* or *M. sativa*.

8. The microorganism according to claim 1, wherein
the nucleic acid section (a) comprises a nucleotide sequence according to SEQ ID NO:1, or
the nucleic acid section (a') comprises a nucleotide sequence according to SEQ ID NO:6 or SEQ ID NO:7, or
the nucleic acid section (b) comprises a nucleotide sequence according to SEQ ID NO:2 or SEQ ID NO:5.

9. The microorganism according to claim 1, wherein the
the bacterial chalcone isomerase comprises an amino acid sequence according to SEQ ID NO:3, or
the plant chalcone isomerase comprises an amino acid sequence according to SEQ ID NO:8 or SEQ ID NO:9, or
the bacterial enoate reductase comprises an amino acid sequence according to SEQ ID NO:4.

10. A vector containing:
a nucleic acid section (a), comprising a gene coding for a bacterial chalcone isomerase, or a nucleic acid section (a'), comprising a gene coding for a plant chalcone isomerase, or both nucleic acid section (a) and nucleic acid section (a');
and
a nucleic acid section (b), comprising a gene coding for an enoate reductase from *E. ramulus* operative to form a dihydrochalcone as a product.

11. The vector of claim 10, wherein the vector is a plasmid vector.

12. The vector according to claim 10, wherein
the gene coding for a bacterial chalcone isomerase codes for a chalcone isomerase from *E. ramulus*, or
the gene coding for a plant chalcone isomerase codes for a chalcone isomerase from *A. thaliana* or *M. sativa*.

13. The vector according to claim 10, wherein
the nucleic acid section (a) comprises a nucleotide sequence according to SEQ ID NO:1, or
the nucleic acid section (a') comprises a nucleotide sequence according to SEQ ID NO:6 or SEQ ID NO:7, or
the nucleic acid section (b) comprises a nucleotide sequence according to SEQ ID NO:2 or SEQ ID NO:5.

14. The vector according to claim 10, wherein
the bacterial chalcone isomerase comprises an amino acid sequence according to SEQ ID NO:3, or
the plant chalcone isomerase comprises an amino acid sequence according to SEQ ID NO:8 or SEQ ID NO:9, or
the bacterial enoate reductase is comprised comprises an amino acid sequence according to SEQ ID NO:4.

15. A host cell containing one or more identical or different vectors according to claim 10.

16. A host cell containing one or more identical or different vectors according to claim 11, and wherein said host cell is a microorganism.

17. A host cell containing one or more vectors with a nucleic acid section
(a), comprising a gene coding for a bacterial chalcone isomerase, or a nucleic acid section (a'), comprising a gene coding for a plant chalcone isomerase, or both nucleic acid section (a) and nucleic acid section (a'); and
one or more vectors with a nucleic acid section (b), comprising a gene coding for an enoate reductase from *E. ramulus* operative to form a dihydrochalcone as a product.

18. Method for production of a dihydrochalcone using a transgenic microorganism comprising:
(i) providing a transgenic microorganism containing transgenes, said transgenes comprising
a nucleic acid section (a), comprising a gene coding for a bacterial chalcone isomerase, or a nucleic acid section (a'), comprising a gene coding for a plant chalcone isomerase, or both nucleic acid section (a) and nucleic acid section (a');
and
a nucleic acid section (b), comprising a gene coding for an enoate reductase from *E. ramulus* operative to form a dihydrochalcone as a product;
(ii) adding one or more flavanones and optionally one or more precursors or one or more derivatives thereof to the transgenic microorganism and cultivation of the transgenic microorganism under conditions which allow the conversion of the flavanone(s) and/or the precursor(s) or of the derivative(s) thereof to a dihydrochalcone; and
(iii) optionally isolating and purifying the dihydrochalcone.

19. The method of claim 18, wherein: the dihydrochalcone is phloretin; and the flavanones are naringin.

20. Method of claim 18, wherein the transgenic microorganism is not a microorganism of the phylum Firmicutes.

21. Method of claim 18, wherein the transgenic microorganism is selected from the group consisting of facultative anaerobic microorganisms, facultative aerobic bacteria, proteobacteria, enterobacteria, *E. coli*, *E. coli* Rosetta, *E. coli* BL21 and *E. coli* SE1, yeasts, *S. cerevesiae* and *P. pastoris*.

22. Method of claim 18, wherein the gene coding for a bacterial chalcone isomerase codes for a chalcone isomerase from a microorganism from the phylum Firmicutes.

23. Method of claim 18, wherein the gene coding for a plant chalcone isomerase codes for a chalcone isomerase from *A. thaliana* or *M. Sativa*.

24. Method of claim 18, wherein the nucleic acid section (a) is comprised of a nucleotide sequence according to SEQ ID NO: 1 or a nucleotide sequence with a nucleotide sequence identity of 95% or more for SEQ ID NO:1.

25. Method of claim 18, wherein the nucleic acid section (a') is comprised of a nucleotide sequence according to SEQ ID NO:6 or SEQ ID NO:7 or a nucleotide sequence with a nucleotide sequence identity of 95% or more for SEQ ID NO:6 or SEQ ID NO:7.

26. Method of claim 18, wherein the nucleic acid section (b) is comprised of a nucleotide sequence according to SEQ ID NO:2 or SEQ ID NO:5 or a nucleotide sequence with a nucleotide sequence identity of 95% or more for SEQ ID NO:2 or SEQ ID NO:5.

27. Method of claim 18, wherein the bacterial chalcone isomerase is comprised of an amino acid sequence according to SEQ ID NO:3 or an amino acid sequence with an amino acid sequence identity of 95% or more for SEQ ID NO:3.

28. Method of claim 18, wherein the plant chalcone isomerase is comprised of an 20 amino acid sequence according to SEQ ID NO:8 or SEQ ID NO:9 or an amino acid sequence with an amino acid sequence identity of 95% or more for SEQ ID NO:8 or SEQ ID NO:9.

29. Method of claim 18, wherein the bacterial enoate reductase is comprised of an amino acid sequence according to SEQ ID NO:4 or an amino acid sequence with an amino acid sequence identity of 95% or more for SEQ ID NO:4.

30. Method for production of a dihydrochalcone using a transgenic microorganism, comprising the following steps:
   (i) providing a transgenic microorganism containing transgenes, said transgenes comprising
      a nucleic acid section (a), comprising a gene coding for a bacterial chalcone isomerase, or a nucleic acid section (a'), comprising a gene coding for a plant chalcone isomerase, or both nucleic acid section (a) and nucleic acid section (a'); and
      a nucleic acid section (b), comprising a gene coding for an enoate reductase from E. ramulus operative to form a dihydrochalcone as a product
   (ii) adding one or more flavanones and optionally one or more precursors or one or more derivatives thereof, to the transgenic microorganism and cultivation of the transgenic microorganism under conditions which allow the conversion of the flavanone(s) and/or the precursor(s) or of the derivative(s) thereof to a dihydrochalcone; and
   (iii) isolating and purifying the dihydrochalcone.

31. Method according to claim 30, wherein the transgenic microorganism is not a microorganism of the phylum Firmicutes.

32. Method according to claim 30, wherein in step (ii) naringin and/or an aglycone thereof is or are added.

33. Method according to claim 30, wherein
the gene coding for a bacterial chalcone isomerase codes for a chalcone isomerase from a microorganism from the phylum Firmicutes, and/or
the gene coding for a plant chalcone isomerase codes for a chalcone isomerase from A. thaliana or M. sativa.

34. Method according to claim 30, wherein
the nucleic acid section (a) is comprised of a nucleotide sequence according to SEQ ID NO:1 or a nucleotide sequence with a nucleotide sequence identity of 95% or more for SEQ ID NO:1,
and/or
the nucleic acid section (a') is comprised or consists of a nucleotide sequence according to SEQ ID NO: 6 or SEQ ID NO:7 or a nucleotide sequence with a nucleotide sequence identity of 95% or more for SEQ ID NO:6 or SEQ ID NO:7,
and/or
the nucleic acid section (b) is comprised of a nucleotide sequence according to SEQ ID NO:2 or SEQ ID NO:5 or a nucleotide sequence with a nucleotide sequence identity of 95% or more for SEQ ID NO:2 or SEQ ID NO:5.

35. Method according to claim 30, wherein
the bacterial chalcone isomerase is comprised of an amino acid sequence according to SEQ ID NO:3 or an amino acid sequence with an amino acid sequence identity of 95% or more for SEQ ID NO:3,
and/or
the plant chalcone isomerase is comprised of an amino acid sequence according to SEQ ID NO: 8 or SEQ ID NO:9 or an amino acid sequence with an amino acid sequence identity of 95% or more for SEQ ID NO:8 or SEQ ID NO:9,
and/or
the bacterial enoate reductase is comprised of an amino acid sequence according to SEQ ID NO:4 or an amino acid sequence with an amino acid sequence identity of 95% or more for SEQ ID NO:4.

36. The method according to claim 30, wherein the microorganism is not Eubacterium ramulus.

37. The method according to claim 30, wherein the microorganism is selected from the group consisting of facultative anaerobic microorganisms.

38. The method according to claim 30, wherein the microorganism is selected from the group consisting of enterobacteria and yeasts.

39. The method of claim 30, wherein the dihydrochalcone is phloretin; and the flavanones are naringin.

* * * * *

SEQUENCE LISTING

<160> NUMBER OF SEQ ID NOS: 9

<210> SEQ ID NO 1
<211> LENGTH: 852
<212> TYPE: DNA
<213> ORGANISM: Eubacterium ramulus

<400> SEQUENCE: 1

```
atggcagatt tcaaattcga accaatgaga agtcttatct acgttgactg cgtaagcgaa      60
gactacagac caaaacttca gagatggatt tataaagtac atattccgga cagcatctct     120
cagtttgagc cgtatgttac caaatatgca ttttatccgt ccttcccgat tccaccacag     180
ggtgatcgtt tcggatacgc aagaatgcag ctgacagagc atcactggtt agtaagcgac     240
cttgatcctc gtcttgagat caaagcaatc gctgagacat tcccgatgga cgtacttgta     300
tggcagggac agatcccggc agcagctcat acagacgctc agatcgattc tgacggagat     360
```

```
gcaggaaatg cagcccgtaa atccaacaat gcagaaggaa atccatttat ctttgcattc    420
cttccgatgt ggtgggagaa agacctgaaa ggaaaaggac gtacgatcga ggacggcgca    480
aactatcgtt tcaatatgac tatcggtttc ccagaaggcg tagacaaagc agagggagag    540
aaatggttat ttgagaaagt agttccgatt cttcaggcag ctccggagtg tacacgtgta    600
cttgcaagtg ccgtaaagaa agacatcaac ggatgcgtaa tggattgggt acttgaaatc    660
tggtttgaga atcagtccgg atggtacaaa gtaatggtag atgacatgaa agcacttgaa    720
aaaccgtcat gggctcagca ggatgctttc ccgttcctga aaccatacca caatgtttgc    780
agtgcagcag ttgctgatta tacaccaagc aacaaccttg caaattatcg tggatacatc    840
accatgagat aa                                                        852

<210> SEQ ID NO 2
<211> LENGTH: 2037
<212> TYPE: DNA
<213> ORGANISM: Eubacterium ramulus

<400> SEQUENCE: 2
atggcagaaa aaaatcagta ttttccacat ttgtttgagc cgttaaaagt tggttcaaag     60
acaattaaga accgtattga ggcagcaccg gctttatttg cattcgagca ttatatcgaa    120
ctgaatccgg atccgtttgg ctataccaca ccggttccgg agcgtgcgtt ccgtatgctg    180
gaggcaaagg caaaggagg ggcaggaatt gtatgtctgg gtgagttaag cccgaatcat    240
gagtatgaca acggtttcc gtttgaaccg tatcttgatt ttacatccag atcagataag    300
cagtttgaaa ttatgaagga aactgcggag atgatcaaaa gctatggggc atttccgatg    360
ggcgagctgc tttcctgcgg tgaaatcaag acaaatatcg gagatggtat caatccgaag    420
ggaccatctg agaaagatct tccggatggc tctcatgtgg aggcgtttac aaaagaagag    480 atttttaagct gctatcagga ttatgtaact gcatgtaaat ggtttcaggc agcaggctgg    540
gaaggcatta tgatccactg cggacatggc tggcttccgg cacagttcct gtctccgcaa    600
tacaataaac gtaccgatga gtatggtgga tcttttgaaa acagagcaag atttactgtt    660
gatctgttaa aaactgttcg tgaagctatg ggaccggact tcgtgatcga gatccgtgtc    720
agcagctctg agcatttacc gggcggatta gagctggaag atgctgtaaa ttattgtaaa    780
ctgtgtgagc catacattga tatgatccat gtctcctgtg gtcattacct gagttcttcc    840
agaagttggg agttcacaac tgcttatgca ccgcatggtc cgaatattga accggcagct    900
gttatcaaac agaacgtatc cattccggtt gcggcagtcg gcggcatcaa ttctccggaa    960
caggcggaag aggcaatcgc gtcaggaaaa atcgatatgg tatccatggg acgtcagttc   1020
tttgcagatc cggcatttcc aaacaaggca aagaagggc atgcagatga gatccgtcgc   1080
tgtctgcgct gcggaagatg ctatccgggt ccgtccggcg agcatgaaac agagatctgg   1140
acggtgaaat tccaccact ggattcctgt accatcaatc catatgatgt atggccggca   1200
tctcatcata aagtccttcc ggaccgcatg ccgaaaccgg aagcaagccg taaggtattg   1260
gtagtaggcg gcggctgtgg cggtctgcag acagcgatca cagcatcaga cagaggtcat   1320
caggtaatcc tgtgcgaaaa atccggagta ttaggcggtc tgatcaattt tacgatcat   1380 acggatcata agtagatat cagaaacttc aaagatctgc tgatccgcga tgtggagaaa   1440
cgtccgatcg aagtaagatt aaactgtgaa gtaacaccgg aactcatcag agaaattgct   1500
ccggaagcag ttgtactggc cgtcggatcc gatgatctga tccttccaat cgagggaatt   1560
```

-continued

```
gaaaatgcgg taacagcaat ggacgtatac agcaatgact ttgcaggtct tggaaagagc    1620
accatcgtac tcggtggcgg tctggttggc tgtgaggcag ccgcagatta tattgatcac    1680
ggtgtagaga caacgattgt tgaaatgaaa ggtgcgctga tgccggagac aaccggtctg    1740
taccgtacag ctgtacatga tttcatcgac aaaaacggcg gcaaatacga agtaaatgca    1800
aaagttgtca agttggcaa agattttgtg gtagcggaac aagatgggaa agagattacc    1860
atcaaagcag attctgttgt caatgcaatg gacgccgtg cgcatgcgac agaagcactt    1920
gagacagcta tcaaagaagc tggtattccg gtatggaaga tcggtgactg tgtccgtgcg    1980
cgtcagatcg gtgatgcggt aagagaaggc tggaccgcag caatggaaat tatctaa      2037
```

<210> SEQ ID NO 3
<211> LENGTH: 283
<212> TYPE: PRT
<213> ORGANISM: Eubacterium ramulus

<400> SEQUENCE: 3

```
Met Ala Asp Phe Lys Phe Glu Pro Met Arg Ser Leu Ile Tyr Val Asp
1               5                   10                  15

Cys Val Ser Glu Asp Tyr Arg Pro Lys Leu Gln Arg Trp Ile Tyr Lys
            20                  25                  30

Val His Ile Pro Asp Ser Ile Ser Gln Phe Glu Pro Tyr Val Thr Lys
        35                  40                  45

Tyr Ala Phe Tyr Pro Ser Phe Pro Ile Pro Pro Gln Gly Asp Arg Phe
    50                  55                  60

Gly Tyr Ala Arg Met Gln Leu Thr Glu His His Trp Leu Val Ser Asp
65                  70                  75                  80

Leu Asp Pro Arg Leu Glu Ile Lys Ala Ile Ala Glu Thr Phe Pro Met
                85                  90                  95

Asp Val Leu Val Trp Gln Gly Gln Ile Pro Ala Ala His Thr Asp
            100                 105                 110

Ala Gln Ile Asp Ser Asp Gly Asp Ala Gly Asn Ala Ala Arg Lys Ser
        115                 120                 125

Asn Asn Ala Glu Gly Asn Pro Phe Ile Phe Ala Phe Leu Pro Met Trp
    130                 135                 140

Trp Glu Lys Asp Leu Lys Gly Lys Gly Arg Thr Ile Glu Asp Gly Ala
145                 150                 155                 160

Asn Tyr Arg Phe Asn Met Thr Ile Gly Phe Pro Glu Gly Val Asp Lys
                165                 170                 175

Ala Glu Gly Glu Lys Trp Leu Phe Glu Lys Val Val Pro Ile Leu Gln
            180                 185                 190

Ala Ala Pro Glu Cys Thr Arg Val Leu Ala Ser Ala Val Lys Lys Asp
        195                 200                 205

Ile Asn Gly Cys Val Met Asp Trp Val Leu Glu Ile Trp Phe Glu Asn
    210                 215                 220

Gln Ser Gly Trp Tyr Lys Val Met Val Asp Met Lys Ala Leu Glu
225                 230                 235                 240

Lys Pro Ser Trp Ala Gln Gln Asp Ala Phe Pro Phe Leu Lys Pro Tyr
                245                 250                 255

His Asn Val Cys Ser Ala Ala Val Ala Asp Tyr Thr Pro Ser Asn Asn
            260                 265                 270

Leu Ala Asn Tyr Arg Gly Tyr Ile Thr Met Arg
        275                 280
```

<210> SEQ ID NO 4
<211> LENGTH: 678
<212> TYPE: PRT
<213> ORGANISM: Eubacterium ramulus

<400> SEQUENCE: 4

```
Met Ala Glu Lys Asn Gln Tyr Phe Pro His Leu Phe Glu Pro Leu Lys
1               5                   10                  15

Val Gly Ser Lys Thr Ile Lys Asn Arg Ile Glu Ala Ala Pro Ala Leu
            20                  25                  30

Phe Ala Phe Glu His Tyr Ile Glu Leu Asn Pro Asp Pro Phe Gly Tyr
        35                  40                  45

Thr Thr Pro Val Pro Glu Arg Ala Phe Arg Met Leu Glu Ala Lys Ala
    50                  55                  60

Lys Gly Gly Ala Gly Ile Val Cys Leu Gly Glu Leu Ser Pro Asn His
65                  70                  75                  80

Glu Tyr Asp Lys Arg Phe Pro Phe Glu Pro Tyr Leu Asp Phe Thr Ser
                85                  90                  95

Arg Ser Asp Lys Gln Phe Glu Ile Met Lys Glu Thr Ala Glu Met Ile
            100                 105                 110

Lys Ser Tyr Gly Ala Phe Pro Met Gly Glu Leu Leu Ser Cys Gly Glu
        115                 120                 125

Ile Lys Thr Asn Ile Gly Asp Gly Ile Asn Pro Lys Gly Pro Ser Glu
    130                 135                 140

Lys Asp Leu Pro Asp Gly Ser His Val Glu Ala Phe Thr Lys Glu Glu
145                 150                 155                 160

Ile Leu Ser Cys Tyr Gln Asp Tyr Val Thr Ala Cys Lys Trp Phe Gln
                165                 170                 175

Ala Ala Gly Trp Glu Gly Ile Met Ile His Cys Gly His Gly Trp Leu
            180                 185                 190

Pro Ala Gln Phe Leu Ser Pro Gln Tyr Asn Lys Arg Thr Asp Glu Tyr
        195                 200                 205

Gly Gly Ser Phe Glu Asn Arg Ala Arg Phe Thr Val Asp Leu Leu Lys
    210                 215                 220

Thr Val Arg Glu Ala Met Gly Pro Asp Phe Val Ile Glu Ile Arg Val
225                 230                 235                 240

Ser Ser Ser Glu His Leu Pro Gly Gly Leu Glu Leu Glu Asp Ala Val
                245                 250                 255

Asn Tyr Cys Lys Leu Cys Glu Pro Tyr Ile Asp Met Ile His Val Ser
            260                 265                 270

Cys Gly His Tyr Leu Ser Ser Arg Ser Trp Glu Phe Thr Thr Ala
        275                 280                 285

Tyr Ala Pro His Gly Pro Asn Ile Glu Pro Ala Ala Val Ile Lys Gln
    290                 295                 300

Asn Val Ser Ile Pro Val Ala Ala Val Gly Gly Ile Asn Ser Pro Glu
305                 310                 315                 320

Gln Ala Glu Glu Ala Ile Ala Ser Gly Lys Ile Asp Met Val Ser Met
                325                 330                 335

Gly Arg Gln Phe Phe Ala Asp Pro Ala Phe Pro Asn Lys Ala Lys Glu
            340                 345                 350

Gly His Ala Asp Glu Ile Arg Arg Cys Leu Arg Cys Gly Arg Cys Tyr
        355                 360                 365

Pro Gly Pro Ser Gly Glu His Glu Thr Glu Ile Trp Thr Val Lys Phe
    370                 375                 380
```

```
Pro Pro Leu Asp Ser Cys Thr Ile Asn Pro Tyr Asp Val Trp Pro Ala
385                 390                 395                 400

Ser His His Lys Val Leu Pro Asp Arg Met Pro Lys Pro Glu Ala Ser
            405                 410                 415

Arg Lys Val Leu Val Val Gly Gly Cys Gly Gly Leu Gln Thr Ala
        420                 425                 430

Ile Thr Ala Ser Asp Arg Gly His Gln Val Ile Leu Cys Glu Lys Ser
            435                 440                 445

Gly Val Leu Gly Gly Leu Ile Asn Phe Thr Asp His Thr Asp His Lys
        450                 455                 460

Val Asp Ile Arg Asn Phe Lys Asp Leu Leu Ile Arg Asp Val Glu Lys
465                 470                 475                 480

Arg Pro Ile Glu Val Arg Leu Asn Cys Glu Val Thr Pro Glu Leu Ile
            485                 490                 495

Arg Glu Ile Ala Pro Glu Ala Val Leu Ala Val Gly Ser Asp Asp
        500                 505                 510

Leu Ile Leu Pro Ile Glu Gly Ile Glu Asn Ala Val Thr Ala Met Asp
        515                 520                 525

Val Tyr Ser Asn Asp Phe Ala Gly Leu Gly Lys Ser Thr Ile Val Leu
        530                 535                 540

Gly Gly Gly Leu Val Gly Cys Glu Ala Ala Asp Tyr Ile Asp His
545                 550                 555                 560

Gly Val Glu Thr Thr Ile Val Glu Met Lys Gly Ala Leu Met Pro Glu
            565                 570                 575

Thr Thr Gly Leu Tyr Arg Thr Ala Val His Asp Phe Ile Asp Lys Asn
            580                 585                 590

Gly Gly Lys Tyr Glu Val Asn Ala Lys Val Lys Val Gly Lys Asp
        595                 600                 605

Phe Val Val Ala Glu Gln Asp Gly Lys Glu Ile Thr Ile Lys Ala Asp
        610                 615                 620

Ser Val Val Asn Ala Met Gly Arg Arg Ala His Ala Thr Glu Ala Leu
625                 630                 635                 640

Glu Thr Ala Ile Lys Glu Ala Gly Ile Pro Val Trp Lys Ile Gly Asp
            645                 650                 655

Cys Val Arg Ala Arg Gln Ile Gly Asp Ala Val Arg Glu Gly Trp Thr
            660                 665                 670

Ala Ala Met Glu Ile Ile
        675

<210> SEQ ID NO 5
<211> LENGTH: 2037
<212> TYPE: DNA
<213> ORGANISM: Eubacterium ramulus

<400> SEQUENCE: 5
atggcagaaa agaaccaata cttcccgcac ctgtttgaac cgctgaaagt cggctctaaa      60
accattaaaa atcgcatcga agcagcaccg gccctgtttg cattcgaaca ttatatcgaa     120
ctgaacccgg accgtttggg ttacaccacg ccggtgccgg aacgtgcatt ccgtatgctg     180
gaagccaaag caaaaggcgg tgccggcatt gtttgtctgg gtgaactgag cccgaatcac     240
gaatatgata aacgctttcc ggttcgaacc gtacctggat tttaccagcc gttctgacaaa     300 cagttcgaaa ttatgaaaga aacggcagaa atgatcaaaa gctatggcgc ttttccgatg     360
ggtgaactgc tgtcgtgcgg tgaaatcaaa accaacattg gcgatggtat caatccgaaa     420
```

-continued

| | |
|---|---|
| ggcccgtcag aaaaagatct gccggacggt tcgcatgtgg aagccttcac caaagaagaa | 480 |
| atcctgtcat gttaccagga ttacgttacg gcatgcaaat ggttccaagc ggccggctgg | 540 |
| gaaggtatta tgatccattg tggccacggt tggctgccgg cgcagtttct gagcccgcaa | 600 |
| tataacaaac gcaccgatga atacggcggt tcttttgaaa atcgtgcgcg cttcaccgtc | 660 |
| gatctgctga aaacggtgcg tgaagcgatg ggcccggact tcgtgattga atccgtgtt | 720 |
| agctctagtg aacatctgcc gggcggtctg gaactggaag atgcggtgaa ctattgcaaa | 780 |
| ctgtgtgaac cgtacattga catgatccat gttagttgcg gccactatct gtcctcatcg | 840 |
| cgctcctggg aatttaccac ggcttacgcg ccgcacggtc cgaacatcga accggcagct | 900 |
| gtcattaaac agaatgtgag catcccggtt gcagcagtcg gcggtatcaa ctctccggaa | 960 |
| caagcggaag aagccattgc aagtggcaaa atcgatatgg ttagcatggg ccgtcagttt | 1020 |
| ttcgctgacc cggcgtttcc gaataaagca aaagaaggcc atgctgatga aattcgtcgc | 1080 |
| tgcctgcgtt gtggtcgctg ctatccgggc ccgagtggtg aacacgaaac cgaaatctgg | 1140 |
| acggtgaaat tcccgccgct ggatagttgt accattaacc cgtacgacgt gtggccggca | 1200 |
| tcccatcaca aagttctgcc ggatcgcatg ccgaaaccgg aagcgtcccg taaagttctg | 1260 |
| gtggttggcg gtggctgtgg tggtctgcag accgcaatca cggcatcaga ccgcggccat | 1320 |
| caagtcattc tgtgcgaaaa atcgggtgtg ctgggtggcc tgattaactt taccgatcat | 1380 |
| acggaccaca aagttgatat tcgcaatttc aaagatctgc tgatccgtga cgtcgaaaaa | 1440 |
| cgcccgattg aagttcgtct gaattgtgaa gtcaccccgg aactgattcg tgaaatcgct | 1500 |
| ccggaagcag tcgtgctggc agtgggcagt gatgacctga ttctgccgat cgaaggtatt | 1560 |
| gaaaacgccg ttaccgcaat ggatgtctat agcaatgact tgccggcct gggtaaatct | 1620 |
| acgatcgtgc tgggtggcgg tctggttggc tgcgaagcag ctgcggatta tatcgatcat | 1680 |
| ggcgtggaaa ccacgattgt tgaaatgaaa ggcgcactga tgccggaaac cacgggtctg | 1740 |
| tatcgtaccg ctgtgcacga tttattgac aaaaacggcg gtaaatacga agtcaatgcc | 1800 |
| aaagttgtca agtgggcaa agatttcgtg gttgcagaac aggacggtaa agaaattacc | 1860 |
| atcaaagcgg attctgtcgt gaatgcgatg ggccgtcgcg ctcacgcaac cgaagctctg | 1920 |
| gaaacggcga ttaagaagc cggcatcccg gtttggaaaa ttggtgattg cgtccgtgcc | 1980 |
| cgccaaatcg gtgacgcagt tcgtgaaggc tggacggctg caatggaaat catctaa | 2037 |

<210> SEQ ID NO 6
<211> LENGTH: 897
<212> TYPE: DNA
<213> ORGANISM: Medicago sativa

<400> SEQUENCE: 6

| | |
|---|---|
| atggctgcat caatcaccgc aatcactgtg gagaaccttg aatacccagc ggtggttacc | 60 |
| tctccggtca ccggcaaatc atatttcctc ggtggcgctg gggagagagg attgaccatt | 120 |
| gaaggaaact tcatcaagtt cactgccata ggtgtttatt tggaagatat agcagtggct | 180 |
| tcactagctg ccaaatggaa gggtaaatca tctgaagagt tacttgagac ccttgacttt | 240 |
| tacagagaca tcatctcagg tccctttgaa aagttaatta gagggtcaaa gattagggaa | 300 |
| ttgagtggtc ctgagtactc aaggaaggtt atggagaact gtgtggcaca cttgaaatca | 360 |
| gttggaactt atggagatgc agaagctgaa gctatgcaaa aatttgctga agctttcaag | 420 |
| cctgttaatt ttccacctgg tgcctctgtt ttctacaggc aatcacctga tggaatatta | 480 |
| gggcttagtt tctctccgga tacaagtata ccagaaaagg aggctgcact catagagaac | 540 |

```
aaggcagttt catcagcagt gttggagact atgatcggcg agcacgctgt tccccctgat      600
cttaagcgct gtttagctgc aagattacct gcgttgttga acgagggtgc tttcaagatt      660
ggaaactgat gatgattata ctcctatatc actgcatttc caaaagcgtt gcagcacaag      720
aatgagacca tgaactttt taagtctaca cgtttaattt tttgtatatc tatttaccttt     780 cttattagta tcaataatat gaaatgaaag atcttgcttt ctactcttgt actatttctg      840
tgatagataa tgttaatgag tatcttcatc aataaaagtg atttgttttg tttgttc         897

<210> SEQ ID NO 7
<211> LENGTH: 765
<212> TYPE: DNA
<213> ORGANISM: Arabidopsis thaliana

<400> SEQUENCE: 7
atgtcttcat ccaacgcctg cgcctctccg tcaccgttcc ccgccgtcac gaagcttcat       60
gtagactccg tcacgtttgt accgtccgtc aagtcaccgg cctcctccaa tccattattc      120
ctcggcggcg ccggtgtccg aggccttgat atccaaggta aattcgtgat cttcaccgtc      180
attggagtat acctagaggg taacgccgtt ccttctctat ctgtcaagtg aagggaaaa       240 actacggagg agctaacaga atctatcccg ttcttccgtg aaatagtcac cggtgcgttt      300
gagaagttta tcaaggtgac aatgaaactg ccgttaacgg acaacaata ttcggagaaa       360 gtgacggaga attgtgtggc tatatggaaa caattagggc tttatacgga ctgtgaagct      420
aaagctgtgg agaagttctt ggagatcttc aaggaagaaa cattccctcc cggttcatcg      480
atcctcttcg ctctctcccc taccggctct cttacggttg cgttttcgaa agatgatagt      540
atccctgaaa ccgggatcgc tgtgatcgag aacaaattgt tggcggaggc ggttctggaa      600
tctatcatcg ggaagaacgg tgtgtcacct ggcactaggt taagtgttgc agaaagatta      660
tctcagctaa tgatgaagaa caaggacgaa aaggaagtta gtgatcactc tgttgaggaa      720
aaactagcca aagagaactg agaatgatag attttcttg tgttt                       765

<210> SEQ ID NO 8
<211> LENGTH: 222
<212> TYPE: PRT
<213> ORGANISM: Medicago sativa

<400> SEQUENCE: 8

Met Ala Ala Ser Ile Thr Ala Ile Thr Val Glu Asn Leu Glu Tyr Pro
1               5                   10                  15

Ala Val Val Thr Ser Pro Val Thr Gly Lys Ser Tyr Phe Leu Gly Gly
                20                  25                  30

Ala Gly Glu Arg Gly Leu Thr Ile Glu Gly Asn Phe Ile Lys Phe Thr
            35                  40                  45

Ala Ile Gly Val Tyr Leu Glu Asp Ile Ala Val Ala Ser Leu Ala Ala
        50                  55                  60

Lys Trp Lys Gly Lys Ser Ser Glu Glu Leu Leu Glu Thr Leu Asp Phe
65                  70                  75                  80

Tyr Arg Asp Ile Ile Ser Gly Pro Phe Glu Lys Leu Ile Arg Gly Ser
                85                  90                  95

Lys Ile Arg Glu Leu Ser Gly Pro Glu Tyr Ser Arg Lys Val Met Glu
            100                 105                 110

Asn Cys Val Ala His Leu Lys Ser Val Gly Thr Tyr Gly Asp Ala Glu
        115                 120                 125
```

```
Ala Glu Ala Met Gln Lys Phe Ala Glu Ala Phe Lys Pro Val Asn Phe
    130                 135                 140

Pro Pro Gly Ala Ser Val Phe Tyr Arg Gln Ser Pro Asp Gly Ile Leu
145                 150                 155                 160

Gly Leu Ser Phe Ser Pro Asp Thr Ser Ile Pro Glu Lys Glu Ala Ala
                165                 170                 175

Leu Ile Glu Asn Lys Ala Val Ser Ser Ala Val Leu Glu Thr Met Ile
            180                 185                 190

Gly Glu His Ala Val Ser Pro Asp Leu Lys Arg Cys Leu Ala Ala Arg
        195                 200                 205

Leu Pro Ala Leu Leu Asn Glu Gly Ala Phe Lys Ile Gly Asn
    210                 215                 220

<210> SEQ ID NO 9
<211> LENGTH: 246
<212> TYPE: PRT
<213> ORGANISM: Arabidopsis thaliana

<400> SEQUENCE: 9

Met Ser Ser Ser Asn Ala Cys Ala Ser Pro Ser Phe Pro Ala Val
1               5                   10                  15

Thr Lys Leu His Val Asp Ser Val Thr Phe Val Pro Ser Val Lys Ser
            20                  25                  30

Pro Ala Ser Ser Asn Pro Leu Phe Leu Gly Gly Ala Gly Val Arg Gly
                35                  40                  45

Leu Asp Ile Gln Gly Lys Phe Val Ile Phe Thr Val Ile Gly Val Tyr
50                  55                  60

Leu Glu Gly Asn Ala Val Pro Ser Leu Ser Val Lys Trp Lys Gly Lys
65                  70                  75                  80

Thr Thr Glu Glu Leu Thr Glu Ser Ile Pro Phe Phe Arg Glu Ile Val
                85                  90                  95

Thr Gly Ala Phe Glu Lys Phe Ile Lys Val Thr Met Lys Leu Pro Leu
            100                 105                 110

Thr Gly Gln Gln Tyr Ser Glu Lys Val Thr Glu Asn Cys Val Ala Ile
        115                 120                 125

Trp Lys Gln Leu Gly Leu Tyr Thr Asp Cys Glu Ala Lys Ala Val Glu
    130                 135                 140

Lys Phe Leu Glu Ile Phe Lys Glu Glu Thr Phe Pro Pro Gly Ser Ser
145                 150                 155                 160

Ile Leu Phe Ala Leu Ser Pro Thr Gly Ser Leu Thr Val Ala Phe Ser
                165                 170                 175

Lys Asp Asp Ser Ile Pro Glu Thr Gly Ile Ala Val Ile Glu Asn Lys
            180                 185                 190

Leu Leu Ala Glu Ala Val Leu Glu Ser Ile Gly Lys Asn Gly Val
        195                 200                 205

Ser Pro Gly Thr Arg Leu Ser Val Ala Glu Arg Leu Ser Gln Leu Met
    210                 215                 220

Met Lys Asn Lys Asp Glu Lys Glu Val Ser Asp His Ser Val Glu Glu
225                 230                 235                 240

Lys Leu Ala Lys Glu Asn
                245
```